(12) United States Patent
Yamamoto et al.

(10) Patent No.: US 11,076,837 B2
(45) Date of Patent: Aug. 3, 2021

(54) ULTRASONIC ENDOSCOPE

(71) Applicant: FUJIFILM Corporation, Tokyo (JP)

(72) Inventors: Katsuya Yamamoto, Ashigara-kami-gun (JP); Yasuhiko Morimoto, Ashigara-kami-gun (JP); Satoru Okada, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 379 days.

(21) Appl. No.: 16/197,816

(22) Filed: Nov. 21, 2018

(65) Prior Publication Data
US 2019/0090857 A1    Mar. 28, 2019

Related U.S. Application Data

(63) Continuation of application No. PCT/JP2017/018176, filed on May 15, 2017.

(30) Foreign Application Priority Data

Jun. 30, 2016    (JP) .............................. JP2016-130083

(51) Int. Cl.
*A61B 8/12* (2006.01)
*A61B 8/00* (2006.01)
(Continued)

(52) U.S. Cl.
CPC ................ *A61B 8/546* (2013.01); *A61B 8/12* (2013.01); *A61B 8/4444* (2013.01);
(Continued)

(58) Field of Classification Search
CPC ........... A61B 8/12; A61B 8/44; A61B 5/4444; A61B 8/445; A61B 8/4483; A61B 8/4488; A61B 8/546; B06B 1/0622
See application file for complete search history.

(56) References Cited

U.S. PATENT DOCUMENTS

2008/0312537 A1    12/2008    Hyuga
2009/0062656 A1    3/2009    Hyuga
(Continued)

FOREIGN PATENT DOCUMENTS

CN    101396289 A    4/2009
JP    2000-184497 A    6/2000
(Continued)

OTHER PUBLICATIONS

International Preliminary Report on Patentability and Written Opinion of the International Searching Authority (forms PCT/IB/373, PCT/ISA/237 and PCT/IB/326), dated Jan. 10, 2019, for corresponding International Application No. PCT/JP2017/018176, with a Written Opinion translation.

(Continued)

*Primary Examiner* — Mark D Remaly
(74) *Attorney, Agent, or Firm* — Birch, Stewart, Kolasch & Birch, LLP

(57) ABSTRACT

An ultrasonic endoscope has an ultrasonic vibrator array in which a plurality of ultrasonic vibrators are arrayed; a backing material layer that supports the ultrasonic vibrators; shield cables that each include a signal wire and a shield member for the signal wire; a flexible printed wiring board that extends on a side opposite to the ultrasonic vibrator array with respect to the backing material layer and that includes a ground portion electrically connected to the shield members; and a heat conductive layer that is provided on at least one surface of the flexible printed wiring board and connected to the ground portion, the heat conductive layer dissipating heat generated in the plurality of ultrasonic vibrators to the ground portion.

11 Claims, 10 Drawing Sheets

(51) Int. Cl.
 *B06B 1/06* (2006.01)
 *A61B 1/12* (2006.01)
(52) U.S. Cl.
 CPC .......... *A61B 8/4483* (2013.01); *A61B 8/4488* (2013.01); *A61B 8/4494* (2013.01); *B06B 1/0622* (2013.01); *A61B 1/128* (2013.01)

(56) References Cited

U.S. PATENT DOCUMENTS

2009/0088646 A1  4/2009  Nagano et al.
2014/0046190 A1*  2/2014  Ogawa ................ A61B 8/4444
                                                            600/462
2015/0282783 A1  10/2015  Katsura et al.

FOREIGN PATENT DOCUMENTS

| JP | 2009-60501 A | 3/2009 |
| JP | 2009-82360 A | 4/2009 |
| JP | 2011-229976 A | 11/2011 |
| JP | 5329065 B2 | 10/2013 |

OTHER PUBLICATIONS

International Search Report (form PCT/ISA/210), dated Jul. 25, 2017, for corresponding International Application No. PCT/JP2017/018176, with an English translation.
Chinese Office Action for Chinese Application No. 201780038946.9, dated Nov. 3, 2020, with English translation.
Extended European Search Report, dated Apr. 23, 2019, for European Application No. 17819689.5.

* cited by examiner

ULTRASONIC ENDOSCOPE

CROSS-REFERENCE TO RELATED APPLICATIONS

This application is a Continuation of PCT International Application No. PCT/JP2017/018176 filed on May 15, 2017, which claims priority under 35 U.S.C. § 119(a) to Japanese Patent Application No. 2016-130083 filed on Jun. 30, 2016. The above application is hereby expressly incorporated by reference, in its entirety, into the present application.

BACKGROUND OF THE INVENTION

1. Field of the Invention

The present invention relates to an ultrasonic endoscope and relates, in particular, to an ultrasonic endoscope that has, at a distal end portion thereof, a structure for dissipating heat generated in a super-small sized ultrasonic vibrator used in the ultrasonic endoscope that is to be inserted into a body cavity.

2. Description of the Related Art

An ultrasonic endoscope is provided, at a distal end portion of the endoscope, an ultrasonic observation portion for the purpose of observing, mainly, a gallbladder or a pancreas via digestive tracts. At the distal end portion of the ultrasonic endoscope, heat generation factors such an ultrasonic vibrator and a light source of the endoscope are present. Since the distal end portion of the ultrasonic endoscope is a portion that comes into direct contact with an inner portion of a living body such as a human body, the surface temperature of an insertion part is required to be lower than or equal to a certain temperature for safety reasons, for example, for preventing low-temperature burn.

In addition to the ultrasonic observation portion, an illumination unit, a suction portion, and the like are provided at the distal end portion of the ultrasonic endoscope, similarly to a normal endoscope in which no ultrasonic observation portion is provided. As a result, the distal end portion of the ultrasonic endoscope has a thick outer diameter, which may cause degradation in operability of the ultrasonic endoscope and an increase in the burden of a patient into which the distal end portion of the ultrasonic endoscope is inserted.

Considering above, an ultrasonic endoscope that has means for decreasing the surface temperature of a distal end portion while maintaining the size of the distal end portion to be small is desired. Therefore, various suggestions for dissipating heat generated in an ultrasonic vibrator have been put forward in recent years (refer to JP5329065B and JP2000-184497A).

JP5329065B discloses an ultrasonic endoscope that includes an insertion part having a bendable portion and that has, at the insertion part, a backing material layer that has a front surface on which a plurality of ultrasonic vibrators are arranged, an exterior member that houses the plurality of ultrasonic vibrators at a distal end of the insertion part, and a heat conductive member disposed inside the exterior member and in contact with a rear surface of the backing material layer and an inner surface of the exterior member. In this configuration, the heat generated in the ultrasonic vibrators and conducted to the backing material layer and the heat generated in the backing material layer are conducted to the heat conductive member through the backing material layer, further conducted to the exterior member through the heat conductive member, and dissipated to the outside of the ultrasonic endoscope from the exterior member.

JP2000-184497A discloses an ultrasound probe that has a piezoelectric element that emits ultrasonic waves, a signal electrode that is electrically connected to the piezoelectric element and provided on a back surface of the piezoelectric element, a backing material layer for mechanically supporting the piezoelectric element, a heat conductive member disposed between the signal electrode and the backing material layer, and a dissipation member provided around the backing material layer so as to be in contact with the heat conductive member. In this configuration, the heat generated in the piezoelectric element is dissipated to the dissipation member via the heat conductive member.

SUMMARY OF THE INVENTION

Meanwhile, the technology disclosed in JP05329065B considers only a heat dissipation path that dissipates the heat generated in the ultrasonic vibrators and the backing material layer to the exterior member through the heat conductive member. Thus, the technology disclosed in JP05329065B has a problem in which further improvement of a heat dissipation effect is not expected because only the heat dissipation path to the exterior member is considered for both the heat generated in the ultrasonic vibrator and the heat generated in the backing material layer. In the technology disclosed in JP05329065B, heat is dissipated into a body cavity around the distal end portion of the ultrasonic endoscope because only the heat dissipation path to the exterior member is provided. Therefore, there is a problem in which, when a drive voltage of the ultrasonic vibrators is increased, the temperature around the distal end portion of the ultrasonic endoscope is increased.

Moreover, the technology disclosed in JP2000-184497A is mainly applied to an ultrasound probe to be used in an ultrasound diagnostic apparatus and brought into contact with a living body to perform ultrasonic observation, and thus, the heat conductive member, a dissipation plate, and the like are large. Therefore, an area in which the piezoelectric element and the heat conductive member are in contact with each other is large, and it is consequently possible to ensure heat dissipation. However, there is a problem in which it is difficult to ensure sufficient heat dissipation in an ultrasonic endoscope in which a space inside a distal end portion is small.

To improve accuracy of ultrasonic diagnosis in the ultrasonic endoscope or the ultrasound probe disclosed in JP05329065B or JP2000-184497A, it is necessary to use means for, for example, increasing a transmission output of ultrasonic waves by stacking the ultrasonic vibrators, enhancing reception sensitivity with respect to ultrasonic echoes by increasing the number of disposed ultrasonic vibrators, and increasing the drive voltage of the plurality of ultrasonic vibrators. When such means are used, an amount of heat dissipation from the plurality of ultrasonic vibrators is increased, which may cause an increase in the surface temperature of the insertion part of the ultrasonic endoscope, which is to be brought into contact with an inner wall of a body cavity of a patient, in particular, the surface temperature of the distal end portion of the ultrasonic endoscope at which the plurality of ultrasonic vibrators are disposed.

There has been a problem in which it is extremely difficult to efficiently dissipate the heat generated in the distal end portion of the ultrasonic endoscope while maintaining the diameter of the insertion part of the ultrasonic vibrator and the size of the distal end portion to be small although improving accuracy in ultrasonic diagnosis is desired in addition to improving operability and reducing burdens of patients.

The present invention intends to eliminate the above-described problems of existing technologies and to provide an ultrasonic endoscope that has a heat dissipation structure capable of efficiently dissipating heat generated in ultrasonic vibrators while maintaining the diameter of an insertion part and the size of a distal end portion to be small and that is consequently capable of improving accuracy of ultrasonic diagnosis.

An ultrasonic endoscope has an ultrasonic vibrator array in which a plurality of ultrasonic vibrators are arrayed; a backing material layer that supports the plurality of ultrasonic vibrators; a flexible printed wiring board that extends on a side opposite to the ultrasonic vibrator array with respect to the backing material layer and that includes a plurality of electrode pads that are each electrically connected to a respective one of the plurality of ultrasonic vibrators of the ultrasonic vibrator array; a plurality of shield cables that each include a signal wire electrically connected to a respective one of the plurality of ultrasonic vibrators and that each include a shield member for a respective one of the plurality of signal wires; a wiring portion that includes a plurality of connection portions in which the plurality of signal wires of the plurality of shield cables are each electrically connected to a respective one of the plurality of electrode pads of the flexible printed wiring board; a ground portion that is provided on the flexible printed wiring board and electrically connected to the shield members of the shield cables; and a heat conductive layer that is provided on at least one surface of the flexible printed wiring board and connected to the ground portion, the heat conductive layer dissipating heat generated in the plurality of ultrasonic vibrators to the ground portion.

The heat conductive layer is preferably provided at least at a portion of the flexible printed wiring board extending beyond the backing material layer on the side opposite to the ultrasonic vibrator array with respect to the backing material layer.

The portion of the flexible printed wiring board extending beyond the backing material layer on the side opposite to the ultrasonic vibrator array with respect to the backing material layer is preferably a flat surface portion.

The heat conductive layer is preferably provided on at least one surface of the flexible printed wiring board so as to be thermally connected to the plurality of ultrasonic vibrators of the ultrasonic vibrator array and so as to extend beyond the backing material layer from the ultrasonic vibrator array along the backing material layer to the side opposite to the ultrasonic vibrator array with respect to the backing material layer, the heat conductive layer being connected to the ground portion.

The heat conductive layer is preferably provided on at least one surface of the flexible printed wiring board so as to be at a portion of the flexible printed wiring board extending beyond the backing material layer on the side opposite to the ultrasonic vibrator array with respect to the backing material layer, and the ultrasonic endoscope preferably further has a heat conductive member that thermally connects the plurality of ultrasonic vibrators of the ultrasonic vibrator array and the heat conductive layer to each other.

The heat conductive layer is preferably provided, at the portion of the flexible printed wiring board extending beyond the backing material layer, on only one side opposite to the backing material layer, and the heat conductive member preferably thermally connects, on the one side of the flexible printed wiring board opposite to the backing material layer, the plurality of ultrasonic vibrators and the heat conductive layer to each other.

The heat conductive layer preferably includes two heat conductive layers provided on both surfaces of the flexible printed wiring board, and the heat conductive member preferably thermally connects, on one side of the flexible printed wiring board opposite to the backing material layer, the plurality of ultrasonic vibrators and the heat conductive layer that is provided on the one side to each other, and the two heat conductive layers provided on the both surfaces of the flexible printed wiring board are preferably thermally connected to each other.

The heat conductive layer provided on a surface of the flexible printed wiring board on a side where the wiring portion is present is preferably disposed at a portion excluding the plurality of connection portions of the wiring portion so as to surround the plurality of connection portions.

The flexible printed wiring board includes a plurality of flexible printed wiring boards disposed on the side opposite to the ultrasonic vibrator array with respect to the backing material layer.

The ultrasonic endoscope according to the present invention preferably further includes a second heat conductive member that connects the plurality of heat conductive layers that are each provided on a respective one of the plurality of flexible printed wiring boards to each other.

According to the present invention, it is possible, by providing a distal end portion of an ultrasonic endoscope with a heat dissipation structure, to efficiently dissipate heat generated as a result of driving ultrasonic vibrators, and it is thus possible to increase an output of the ultrasonic vibrators without increasing a burden of a patient as a subject of the ultrasonic endoscope.

DESCRIPTION OF THE PREFERRED EMBODIMENTS

First Embodiment

An ultrasonic endoscope according to the present invention will be described in detail on the basis of a suitable embodiment illustrated in the attached drawings.

Figure 1:
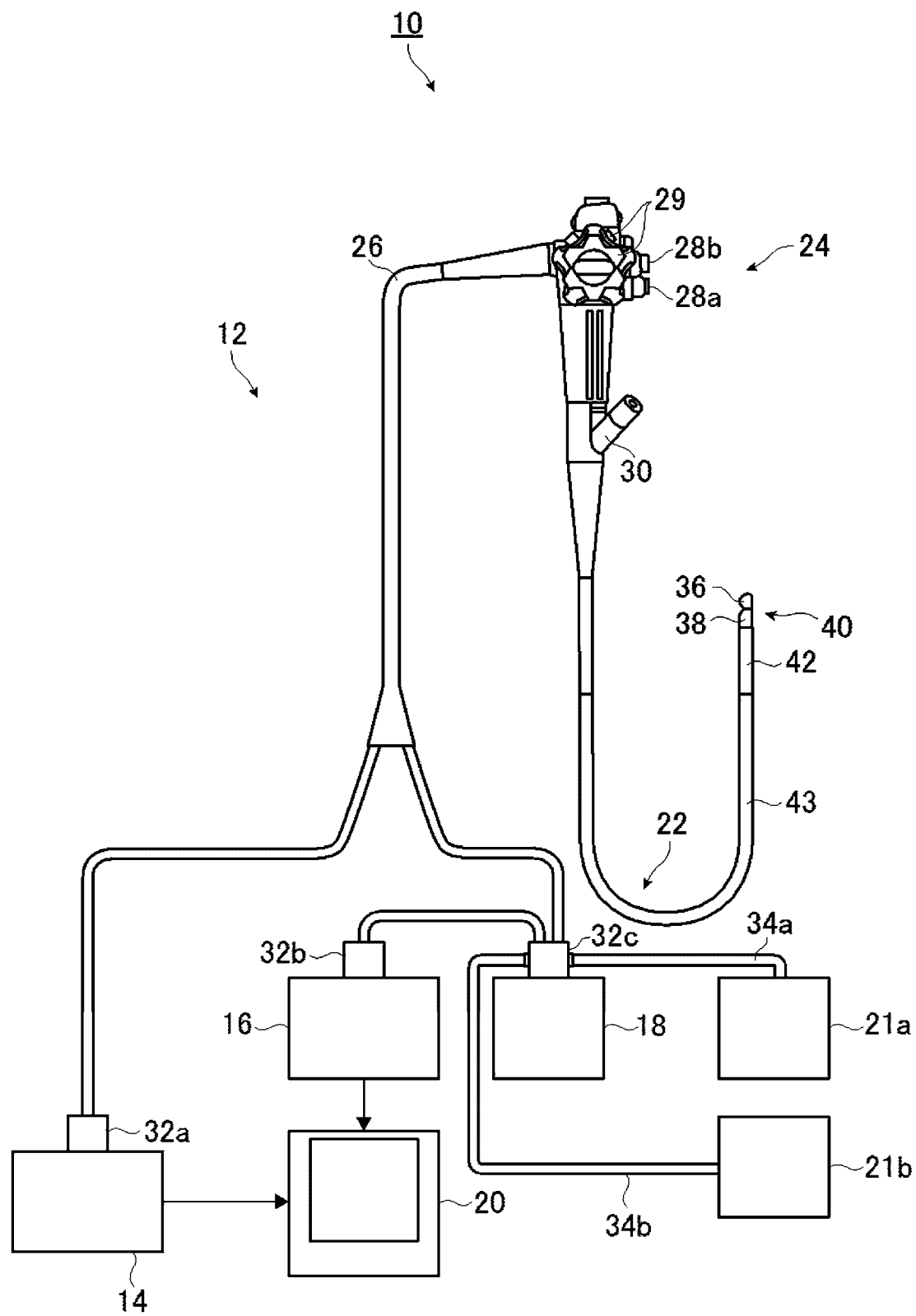
FIG. 1 is a schematic diagram illustrating an example of a configuration of an ultrasonic inspection system that uses an ultrasonic endoscope according to the present invention.

FIG. 1 is a schematic diagram illustrating an example of a configuration of an ultrasonic inspection system that uses the ultrasonic endoscope according to the present invention.

An ultrasonic inspection system 10 illustrated in FIG. 1 enables an observation of a gallbladder or a pancreas, which is difficult to be observed in an ultrasonic inspection from a body surface of a subject such as a patient, to be performed via digestive tracts such as an esophagus, a stomach, a duodenum, a small intestine, and a large intestine, which are body cavities of the subject. In the ultrasonic inspection system 10, an ultrasonic endoscope 12 according to the present invention has an ultrasonic observation portion 36 that acquires an ultrasonic tomographic image (hereinafter referred to as an ultrasound image) and an endoscopic observation portion 38 that acquires an endoscopic optical image (hereinafter referred to as an endoscopic image), and the ultrasonic endoscope 12 is inserted into a body cavity of a subject to acquire an ultrasound image of an observation target part of the subject while observing an endoscopic image of the subject.

As illustrated in FIG. 1, the ultrasonic inspection system 10 includes the ultrasonic endoscope 12 that has a heat dissipation structure, which is a characteristic of the present invention, an ultrasonic processor 14 that generates an ultrasound image, an endoscope processor 16 that generates an endoscopic image, a light source device 18 that supplies illumination light for illuminating an inner portion of a body cavity to the ultrasonic endoscope 12, and a monitor 20 that displays an ultrasound image and/or an endoscopic image.

In addition, the ultrasonic inspection system 10 further includes a water supply tank 21a that stores cleaning water or the like and a suction pump 21b that suctions a suction object (including supplied cleaning water or the like) inside the body cavity. While no illustration is provided, the ultrasonic inspection system 10 may further include a supply pump or the like that supplies the cleaning water inside the water supply tank 21a or a gas such as outside air into a pipe line (not illustrated) inside the ultrasonic endoscope 12.

The ultrasonic endoscope 12 illustrated in FIG. 1 has, at the distal end thereof, the ultrasonic observation portion 36 having the heat dissipation structure, which is a characteristic of the present invention, and the endoscopic observation portion 38, and acquires each of an ultrasound image (echo signal) and an endoscopic image (image signal) by capturing an inner portion of a body cavity of a subject.

The ultrasonic endoscope 12 is constituted by an insertion part 22 that is to be inserted into a body cavity of a subject, the insertion part 22 including the ultrasonic observation portion 36 and the endoscopic observation portion 38 at the distal end thereof, an operating part 24 for operation by an operator such as a doctor and an engineer, the operating part 24 being provided at the proximal end portion of the insertion part 22 so as to be continuous therewith, and a universal cord 26 that has one end connected to the operating part 24.

The operating part 24 is provided with an air-water supply button 28a that opens and closes an air-water supply pipe line (not illustrated) from the water supply tank 21a and a suction button 28b that opens and closes a suction pipe line (not illustrated) from the suction pump 21b, the air-water supply button 28a and the suction button 28b being arranged parallel to each other, a pair of angle knobs 29 and 29, and a treatment tool insertion port (forceps port) 30.

The water supply tank 21a is for storing the cleaning water that is to be supplied into the air-water supply pipe line inside the ultrasonic endoscope 12 to, for example, clean the endoscopic observation portion 38 and the like of the ultrasonic endoscope 12. The air-water supply button 28a is used to cause a gas such as air and water such as the cleaning water that are supplied from the water supply tank 21a via the air-water supply pipe line to spout out from the endoscopic observation portion 38 on the distal end side of the insertion part 22.

The suction pump 21b suctions the suction pipe line (not illustrated) to suction a suction object (including supplied cleaning water and the like) inside a body cavity from the distal end side of the ultrasonic endoscope 12. The suction button 28b is used to suction a suction object inside a body cavity from the distal end side of the insertion part 22 by using the suction force of the suction pump 21b.

The treatment tool insertion port 30 is for inserting therethrough a treatment tool such as forceps, a puncture needle, or a high-frequency knife.

The other end portion of the universal cord 26 is provided with an ultrasonic connector 32a connected to the ultrasonic processor 14, an endoscope connector 32b connected to the endoscope processor 16, and a light source connector 32c connected to the light source device 18. The ultrasonic endoscope 12 is detachably connected to each of the ultrasonic processor 14, the endoscope processor 16, and the light source device 18 via these connectors 32a, 32b, and 32c. An air-water supply tube 34a to which the water supply tank 21a is connected, a suction tube 34b to which the suction pump 21b is connected, and the like are connected to the light source connector 32c.

The insertion part 22 is constituted by, in order from the distal end side, a distal end portion (tip rigid part) 40 formed of a rigid member and having the ultrasonic observation portion 36 and the endoscopic observation portion 38; a bendable bending portion 42 that is provided on the proximal end side of the distal end portion 40 so as to be continuous therewith and that is formed of a plurality of bending pieces that are connected together; and a long and narrow flexible soft portion 43 that connects the proximal end side of the bending portion 42 and the distal end side of the operating part 24 to each other.

The bending portion 42 is remotely operated to bend when the pair of angle knobs 29 and 29 provided at the operating part 24 are rotated. Thus, it is possible to direct the distal end portion 40 in a desired direction.

A balloon in which an ultrasonic transmission medium (for example, water, oil, or the like) is injected and covering the ultrasonic observation portion 36 may be detachably attached to the inner portion of the distal end portion 40. Ultrasonic waves and echo signals considerably attenuate in the air; therefore, it is possible to suppress attenuation of ultrasonic waves and echo signals by injecting the ultrasonic transmission medium into the balloon to cause the balloon to expand and bringing the balloon into contact with an observation target part to eliminate the air from a gap between an ultrasonic vibrator (ultrasonic transducer) array (50: refer to FIGS. 2 to 4, FIG. 6, and FIG. 7) of the ultrasonic observation portion 36 and the observation target part.

The ultrasonic processor 14 generates and supplies an ultrasonic signal (data) for causing the ultrasonic vibrator array (50: refer to FIGS. 2 to 4, FIG. 6, and FIG. 7) of the ultrasonic vibrator unit (46: refer to FIGS. 2 to 4, 69: refer to FIG. 6, 72: refer to FIG. 7) of the ultrasonic observation portion 36 at the distal end portion 40 of the insertion part 22 of the ultrasonic endoscope 12 to generate ultrasonic waves. The ultrasonic processor 14 is for receiving and acquiring, at the ultrasonic vibrator array (50), the echo signal (data) reflected by the observation target part to which ultrasonic waves are emitted and generating an ultrasound image to be displayed on the monitor 20 by subjecting the acquired echo signal to various signal (data) processing.

The endoscope processor 16 is for receiving and acquiring, at the endoscopic observation portion 38 at the distal end portion 40 of the insertion part 22 of the ultrasonic endoscope 12, a captured image signal (data) acquired from the observation target part illuminated with the illumination light from the light source device 18, and generating an endoscopic image to be displayed on the monitor 20 by subjecting the acquired image signal to various signal (data) processing and image processing.

Each of the processors 14 and 16 may be constituted by a processor such as a PC (personal computer).

To acquire an image signal by capturing the observation target part inside the body cavity with the use of the endoscopic observation portion 38 of the ultrasonic endoscope 12, the light source device 18 is for generating illumination light such as white light consisting of light of three primary colors, which are red light (R), green light (G), and blue light (B), or light of a specific wavelength, and supplying the illumination light to the ultrasonic endoscope 12 to cause the illumination light to be propagated through a light guide (not illustrated) inside the ultrasonic endoscope 12, to exit from the endoscopic observation portion 38 at the distal end portion 40 of the insertion part 22 of the ultrasonic endoscope 12, and to illuminate the observation target part inside the body cavity.

The monitor 20 receives each video signal generated by the ultrasonic processor 14 and the endoscope processor 16 and displays an ultrasound image or an endoscopic image. It is possible to display only one of the ultrasound image and the endoscopic image on the monitor 20 by switching these images as appropriate or to display both of these images at the same time. A monitor for displaying ultrasound images and a monitor for displaying endoscopic images may be separately provided, and the ultrasound image and the endoscopic image may be displayed in another optional form.

Next, a configuration of the distal end portion 40 of the insertion part 22 of the ultrasonic endoscope 12 according to the present embodiment will be described in detail with reference to FIGS. 2 to 4.

Figure 2:
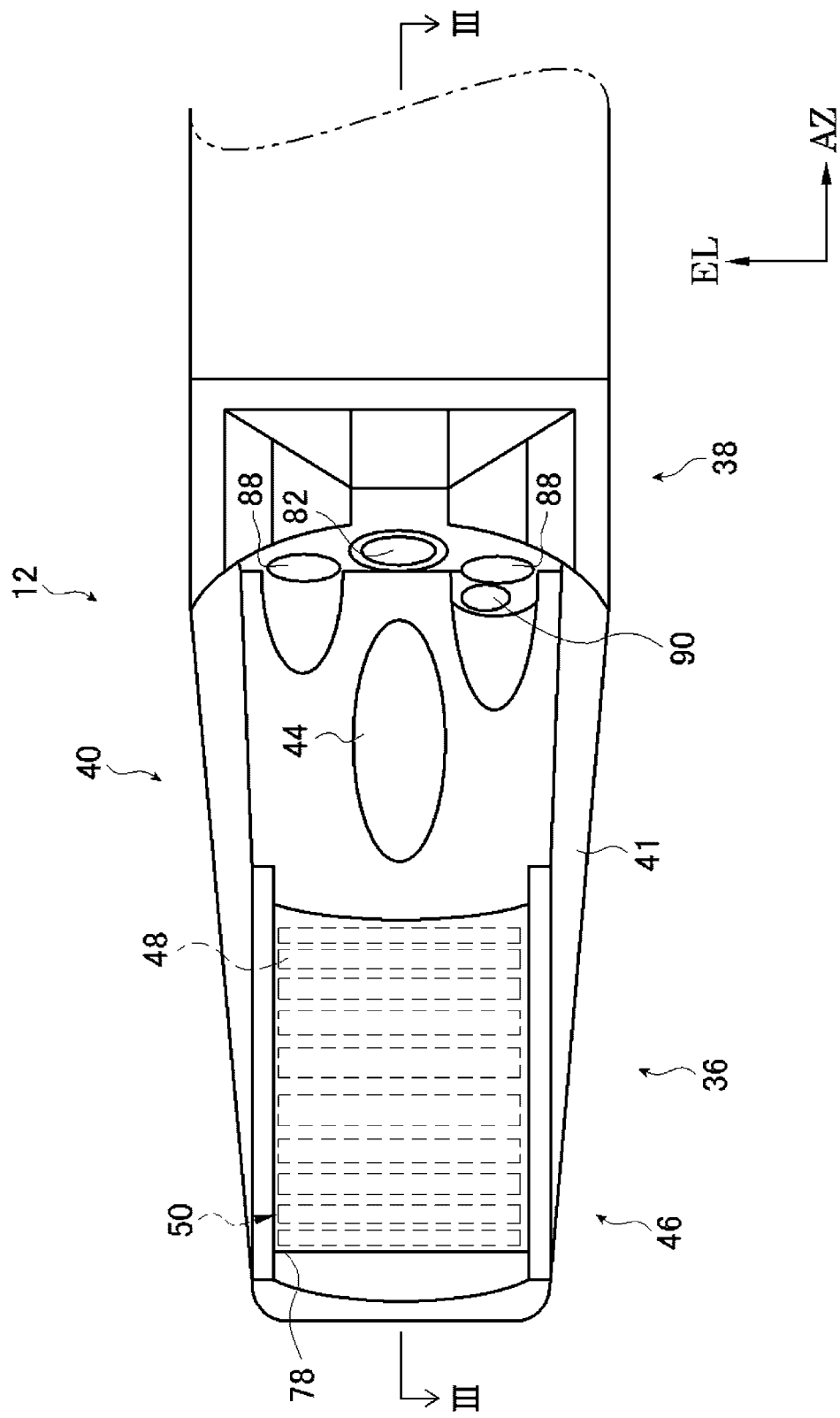
FIG. 2 is a partially enlarged plan view illustrating a distal end portion of an insertion part of the ultrasonic endoscope illustrated in FIG. 1.

FIG. 2 is a partially enlarged plan view illustrating the distal end portion of the ultrasonic endoscope illustrated in FIG. 1 and a portion in the vicinity of the distal end portion. FIG. 3 is a view in the arrow direction of line illustrated in FIG. 2, which is a longitudinal sectional view of the distal end portion of the ultrasonic endoscope illustrated in FIG. 2 taken along the center line thereof in the longitudinal direction. FIG. 4 is a view in the arrow direction of line IV-IV illustrated in FIG. 3, which is a cross-sectional view of the distal end portion of the ultrasonic endoscope illustrated in FIG. 3 taken along the center line of the arc structure of the ultrasonic vibrator array of the ultrasonic observation portion. In FIG. 4, the view is simplified for description, and the coaxial cables (56: refer to FIG. 3) and a connection portion (64: refer to FIG. 3) of the wiring portion (62: refer to FIG. 3) are omitted.

Figure 3:
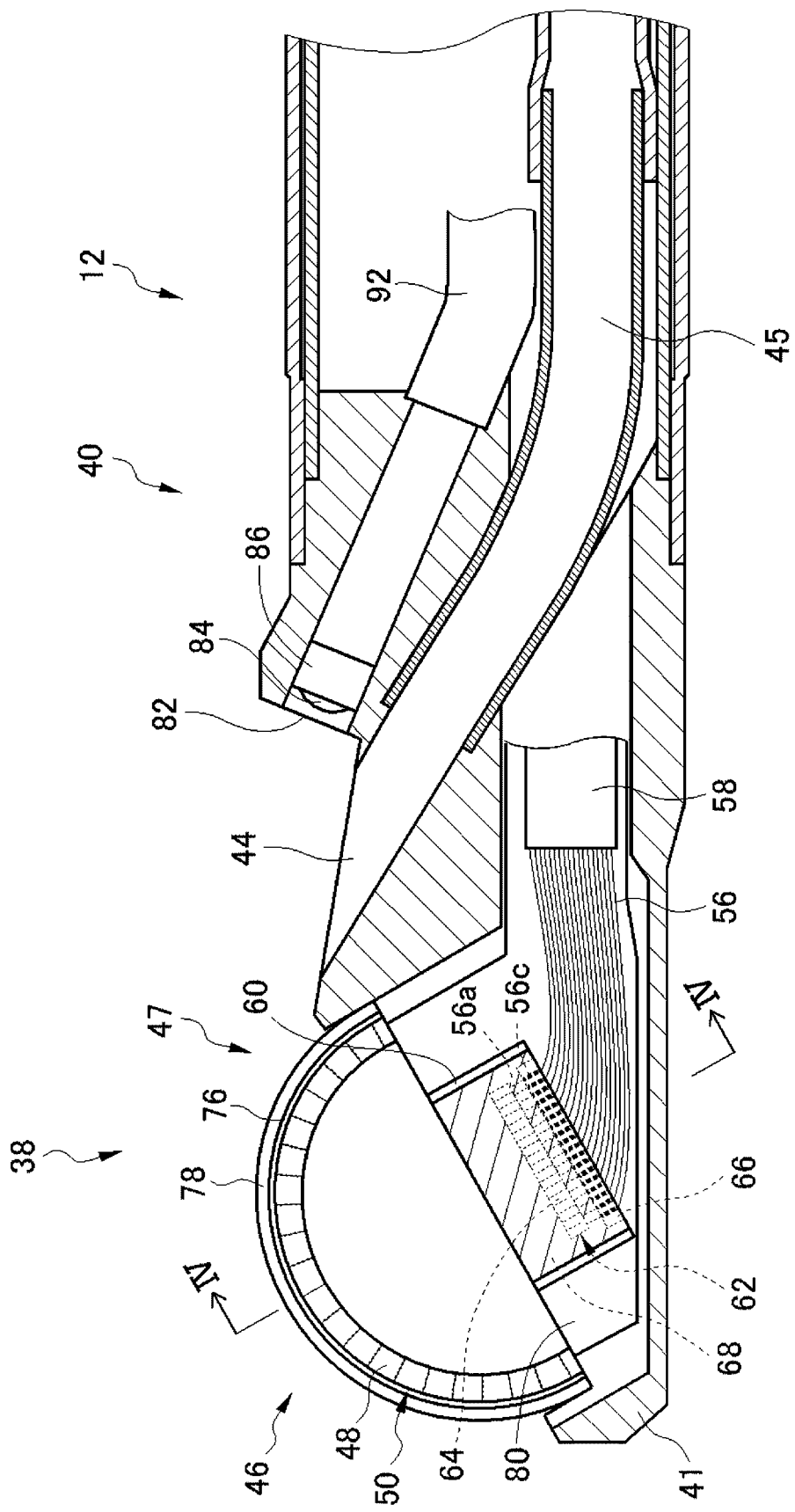
FIG. 3 is a view in the arrow direction of line III-III illustrated in FIG. 2, which is a partial longitudinal sectional view of the distal end portion of the insertion part of the ultrasonic endoscope illustrated in FIG. 2.

As illustrated in FIG. 2 and FIG. 3, the distal end portion 40 of the ultrasonic endoscope 12 is provided with the ultrasonic observation portion 36, on the distal end side, for acquiring an ultrasound image, the endoscopic observation portion 38, on the proximal end side, for acquiring an endoscopic image, and a treatment tool lead-out port 44 between these observation portions. The ultrasonic observation portion 36, the endoscopic observation portion 38, and the treatment tool lead-out port 44 are attached to and held at an exterior member 41 formed of a rigid member such as a rigid resin, the exterior member 41 serving as a distal end main body of the distal end portion 40 of the ultrasonic endoscope 12.

In the example illustrated in FIG. 2, the treatment tool lead-out port 44 is provided between the ultrasonic observation portion 36 and the endoscopic observation portion 38; however the present invention is not particularly limited to the illustrated example, and the treatment tool lead-out port 44 may be provided inside the endoscopic observation portion 38 or may be provided on the proximal end side (bending portion 42 side) of the endoscopic observation portion 38.

Figure 4:
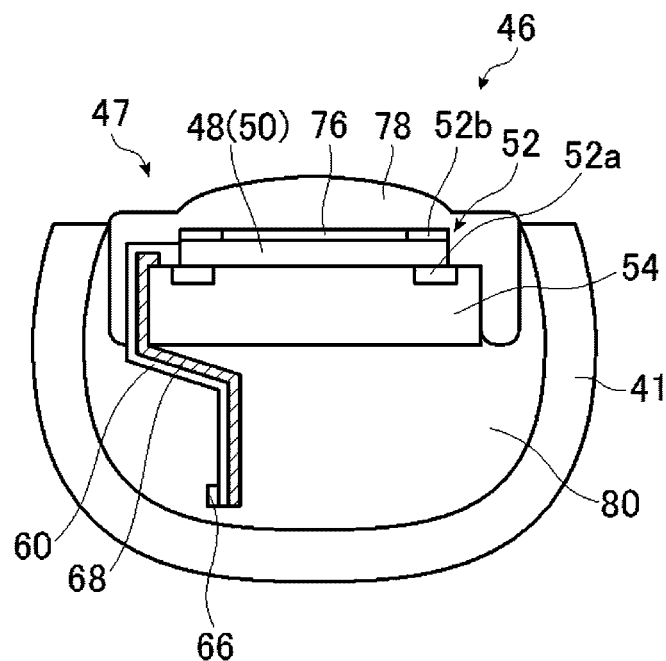
FIG. 4 is a view in the arrow direction of line IV-IV illustrated in FIG. 3, which is a cross-sectional view of an example of an ultrasonic vibrator unit of an ultrasonic observation portion at the distal end portion of the insertion part of the ultrasonic endoscope illustrated in FIG. 3.

As illustrated in FIGS. 2 to 4, the ultrasonic observation portion 36 is constituted by an ultrasonic vibrator unit 46, the exterior member 41 to which the ultrasonic vibrator unit 46 is attached to be held, and a plurality of coaxial cables 56 wired to the ultrasonic vibrator unit 46.

In the example illustrated in FIG. 4, the ultrasonic vibrator unit 46 has an ultrasonic vibrator array 50 formed of a plurality of ultrasonic vibrators (transducers) 48; electrode parts 52 provided on end portion sides of the ultrasonic vibrator array 50 in a width direction; a backing material layer 54 that supports each of the ultrasonic vibrators 48 of the ultrasonic vibrator array 50 from a lower surface side; a flexible printed wiring board (hereinafter simply referred to as the FPC (flexible printed circuit)) 60 disposed along a side surface of the backing material layer 54 in the width direction and electrically connected to the electrode parts 52; a heat conductive layer 68 provided on a surface of the FPC 60 facing the backing material layer 54; and a filler layer 80 that fills a gap between the exterior member 41 and the backing material layer 54. One end of each of the plurality of coaxial cables 56 each having the other end electrically connected to the ultrasonic processor 14 is wired to the FPC 60.

Figure 5:
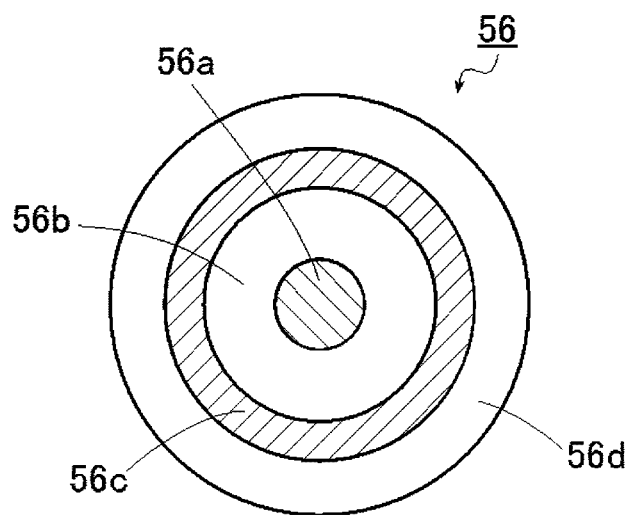
FIG. 5 is a schematic cross-sectional view of a coaxial cable illustrated in FIG. 3.

As illustrated in FIG. 3, the plurality of coaxial cables 56 connected to a wiring portion 62 of the FPC 60 are gathered into a bundle on the proximal end side (universal cord 26 side) of the distal end portion 40 of the insertion part 22 by using an outer sheath 58, and, in wiring, each of the coaxial cables 56 is pulled out and electrically connected to the FPC 60. As illustrated in FIG. 5, the plurality of coaxial cables 56 each include, on the center side thereof, a signal wire 56a electrically connected to a respective one of a plurality of connection portions 64 of the wiring portion 62 of the FPC 60, and each coaxial cable 56 has an insulating outer sheath 56b provided on an outside layer of the signal wire 56a, a conductive shield layer 56c provided on an outside layer of the outer sheath 56b, the shield layer 56c being groundable on the proximal end side (universal cord 26 side) of the ultrasonic endoscope 12, and an insulating outer sheath 56d provided on an outermost layer. Consequently, it is possible to wire the signal wires 56a of the plurality of coaxial cables 56 to the wiring portion 62 without bending the plurality of coaxial cables 56, as is in the example illustrated in FIG. 3, in a case in which the wiring portion 62 is disposed on the backing material layer 54 side of a ground portion 66 in the FPC 60.

Meanwhile, grounding in the present invention is not limited to causing a conductive member to have a zero potential, and the grounding includes maintaining a conductive member at a certain low voltage by, for example, connecting the conductive member to a member that has large electric capacitance.

In the example illustrated in FIG. 3, the coaxial cables 56 are used; however, cables having a configuration different from the above-described configuration of the coaxial cables 56 may be used provided that the cables (shield cables) have signal wires that are electrically connected to the plurality of ultrasonic vibrators 48 and that are used for transmitting and receiving voltage signals and groundable shield members that are electrically connected to a vibrator ground 52b of the plurality of ultrasonic vibrators 48. While no illustration is provided, for example, cables having a known structure such as a cable unit that includes, on the center side thereof, a plurality of signal wires each covered by an insulating outer sheath and a plurality of groundable lead wires, and that has an outer sheath covering the plurality of signal wires and the lead wires are usable as the shield cables. The arrangement of the signal wires and the lead wires of the cable unit is not limited to that described above, and the plurality of signal wires and lead wires may be randomly arranged inside the outer sheath covering the signal wires and the lead wires.

In addition, the ultrasonic vibrator unit 46 has an acoustic matching layer 76 laminated on the ultrasonic vibrator array 50, and an acoustic lens 78 laminated on the acoustic matching layer 76. In other words, the ultrasonic vibrator unit 46 is formed of a laminated body 47 of the acoustic lens 78, the acoustic matching layer 76, the ultrasonic vibrator array 50, and the backing material layer 54.

The acoustic matching layer 76 is for acoustic impedance matching between a subject such as a human body and the ultrasonic vibrators 48.

The acoustic lens 78 mounted on the acoustic matching layer 76 is for causing ultrasonic waves emitted from the ultrasonic vibrator array 50 to be converged toward an observation target part. The acoustic lens 78 is made of, for example, a silicone-based resin (a millable silicone rubber (HTV rubber), a liquid silicone rubber (RTV rubber), etc.), a butadiene-based resin, a polyurethane-based resin, or the like. To increase the transmittance of ultrasonic waves through acoustic impedance matching between a subject and the ultrasonic vibrators 48 in the acoustic matching layer 76, powder of titanium oxide, alumina, silica, or the like is mixed, as necessary, in the acoustic lens 78.

The ultrasonic vibrator array 50 of the ultrasonic vibrator unit 46 is a 48-192 channel (CH) array formed of the plurality of, for example 48 to 192, rectangular parallelepiped ultrasonic vibrators (transducers) 48 arrayed in a convex arc shape facing outward.

In other words, the ultrasonic vibrator array 50 is formed of the plurality of ultrasonic vibrators 48 arrayed, for example, as is in the illustrated example, in a one-dimensional array shape at a predetermined pitch. Thus, the ultrasonic vibrators 48 constituting the ultrasonic vibrator array 50 are arrayed in a convex curved shape at an equal interval in the axial direction (the longitudinal axial direction of the insertion part 22) of the distal end portion 40 and are configured to sequentially driven on the basis of a drive signal input from the ultrasonic processor 14. Accordingly, convex electronic scanning is performed with a scanning region set at a region, illustrated in FIG. 2, in which the ultrasonic vibrators 48 are arrayed.

The ultrasonic vibrator array 50 is shorter, than in a direction (AZ (azimuth) direction) parallel to a bottom surface of the backing material layer 54, in the width direction of the ultrasonic vibrator array 50 orthogonal to the AZ direction, that is, in the longitudinal direction (EL (elevation) direction) of the ultrasonic vibrators 48, and the ultrasonic vibrator array 50 is arranged so as to be inclined such that the rear end portion thereof protrudes. As illustrated in FIG. 4, the ultrasonic vibrators 48 have a configuration in which electrodes are disposed on both surfaces of a thick film of a piezoelectric body made of, for example, PZT (lead zirconate titanate), PVDF (polyvinylidene fluoride), or the like. The electrodes on one side are individual electrodes 52a that are independent from each other for respective ultrasonic vibrators 48, and the electrode on the other side is the vibrator ground (vibrator ground electrode) 52b, which is a common electrode common to all of the ultrasonic vibrators 48. In the illustrated example, the plurality of individual electrodes 52a are disposed on a lower surface of an end portion of the plurality of ultrasonic vibrators 48, and the vibrator ground 52b is provided on an upper surface of the end portion of the ultrasonic vibrators 48. The plurality of individual electrodes 52a and the vibrator ground 52b constitute the electrode parts 52.

Each gap between two ultrasonic vibrators 48 adjacent to each other is filled with a filler such as an epoxy resin.

In the ultrasonic vibrator unit 46 of the ultrasonic observation portion 36, when each of the ultrasonic vibrators 48 of the ultrasonic vibrator array 50 is driven, and a voltage is applied to both electrodes of each ultrasonic vibrator 48, the piezoelectric bodies vibrate to sequentially generate ultrasonic waves, and the ultrasonic waves are emitted toward an observation target part of a subject. Then, a scanning region along a curved surface on which the ultrasonic vibrator array 50 is arranged, for example, a region of tens of millimeters from the center of the curvature of the curved surface is scanned with ultrasonic waves by sequentially driving the plurality of ultrasonic vibrators 48 with the use of an electronic switch such as a multiplexer.

When echo signals (ultrasonic echoes) reflected by the observation target part are received, the piezoelectric bodies vibrate to generate voltages, and the voltages are output as electric signals (ultrasonic wave detection signals) in accordance with the received ultrasonic echoes to the ultrasonic processor 14. After being subjected to various processing in the ultrasonic processor 14, the signals are displayed as an ultrasound image on the monitor 20.

When a drive voltage is applied to the plurality of ultrasonic vibrators 48, and the piezoelectric bodies each constituting a respective one of the plurality of ultrasonic vibrators 48 vibrate to generate ultrasonic waves that are to be transmitted toward an object and when ultrasonic echoes of ultrasonic waves transmitted from the plurality of ultrasonic vibrators 48 and reflected by the object are received by the plurality of ultrasonic vibrators 48, and the piezoelectric bodies vibrate to generate ultrasonic echo signals (voltage signals), as described above, heat is generated in each of the piezoelectric bodies each constituting the respective one of the plurality of ultrasonic vibrators 48. One of means for enhancing definition of an ultrasound image, that is, improving accuracy of ultrasonic diagnosis is means for increasing the output power of the drive signal (voltage signal) of the plurality of ultrasonic vibrators 48; however, as the drive voltage increases, the heat generated in the piezoelectric bodies increases.

Thus, it is possible to efficiently dissipate the heat generated in the piezoelectric bodies by providing the distal end portion 40 of the ultrasonic endoscope 12 with the heat dissipation structure, which is a characteristic of the present invention. Consequently, it is possible to improve the accuracy of ultrasonic diagnosis.

As illustrated in FIGS. 3 and 4, the electrode parts 52 of the ultrasonic vibrator unit 46 are provided in an arc shape, on end surface sides (of ultrasonic vibrators 48) of the ultrasonic vibrator array 50 vertical to the arc-shaped surface formed by the array of the plurality (48 to 192) of ultrasonic vibrators 48, and the electrode parts 52 are formed of the plurality (48 to 192) of individual electrodes 52a that are each electrically connected to a respective one of the plurality (48 to 192) of ultrasonic vibrators 48. The electrode parts 52 include the vibrator ground 52b of the plurality of ultrasonic vibrators 48. Meanwhile, in the present invention, "vertical" is not limited to 90 degrees and includes "substantially vertical", for example, 90 degrees ±5 degrees, that is, an angle within a range from 85 degrees to 95 degrees.

The electrode parts 52 are provided on the end surface sides of the ultrasonic vibrator array 50 vertical to the surface of the array of the ultrasonic vibrators 48; however, when the number of the ultrasonic vibrators 48 is small, the electrode parts 52 may be provided on one of the end surface side. Since it is preferable that the number of the ultrasonic vibrators 48 be large, the plurality of individual electrodes 52a are preferably provided on both outside surfaces of the ultrasonic vibrator array 50. The plurality of individual electrodes 52a may be provided on the center side instead of the end surface sides of the ultrasonic vibrator array 50. When the ultrasonic vibrators 48 are provided in multiple rows, for example, two rows in the width direction, it is possible to efficiently perform wiring, even when the number of channels is large, by providing the plurality of individual electrodes 52a on the center side of the ultrasonic vibrator array 50. Thus providing the plurality of individual electrodes 52a on the center side, in addition to both outside surfaces, of the ultrasonic vibrator array 50 makes it possible to increase the number of the ultrasonic vibrators 48, that is, the number of the channels.

In the example illustrated in FIG. 4, the plurality of individual electrodes 52a are constituted by the individual electrodes 52a provided on the end surface sides of each ultrasonic vibrator 48 in the longitudinal direction; however, the present invention is not limited thereto. The plurality of individual electrodes 52a may be constituted by other electrodes wired and connected to the individual electrodes 52a provided that the other electrodes are electrically connected to the individual electrodes 52a of the ultrasonic vibrators 48, in each case in which the plurality of individual electrodes 52a are provided on the one outside surface, both outside surfaces, or the center side of the ultrasonic vibrator array 50. In addition, instead of directly including the vibrator ground 52b, the electrode parts 52 may include an electrode wired and connected to the vibrator ground 52b. Moreover, the plurality of individual electrodes 52a and the vibrator ground 52b of the electrode parts 52 are preferably provided as electrode pads.

Next, as illustrated in FIGS. 3 and 4, the backing material layer 54 of the ultrasonic vibrator unit 46 is a layer that is disposed on an inner side with respect to the surface of the array of the plurality of ultrasonic vibrators 48, in other words, on a back surface (lower surface) of the ultrasonic vibrator array 50 and that is of a member formed of a backing material. The backing material layer 54 has a role of mechanically and flexibly supporting the ultrasonic vibrator array 50 and attenuating, of ultrasonic signals emitted by the plurality of ultrasonic vibrators 48 or reflected by an observation target and propagated, the ultrasonic waves that are propagated to the backing material layer 54 side. Thus, the backing material is formed of a material, such as a hard rubber, having rigidity, and an ultrasonic wave attenuating material (a ferrite, a ceramic, etc.) is added to the backing material, as necessary.

Therefore, the ultrasonic vibrator array 50 is preferably an array in which the plurality of rectangular parallelepiped ultrasonic vibrators 48 are arrayed on an arc-shaped upper surface that serves as a cross-sectionally convex arc-shaped upper surface of the backing material layer 54 so as to be parallel to each other in the longitudinal direction thereof, preferably at an equal interval, in other words, an array in which the plurality of ultrasonic vibrators 48 are arrayed in an arc shape facing outward.

Provided that the above-described role is fulfilled, the shape of the backing material layer 54 may be a substantially half-cylindrical shape, such as that illustrated in FIG. 3 or FIG. 4 and may be provided with a concave section to enable a portion of the FPC 60 and the heat conductive layer 68 to be housed therein.

The filler layer 80 of the ultrasonic vibrator unit 46, illustrated in FIG. 3 and FIG. 4, fills the gap between the exterior member 41 and the backing material layer 54 and also plays a role of fixing the FPC 60, the coaxial cables 56, and wiring parts of various types. The filler layer 80 preferably has an acoustic impedance that matches with that of the backing material layer 54 with precision of a certain level or higher to suppress ultrasonic signals propagated from the ultrasonic vibrator array 50 to the backing material layer 54 side from being reflected by a boundary surface between the filler layer 80 and the backing material layer 54. In addition, to increase efficiency of dissipating the heat generated in the plurality of ultrasonic vibrators 48, the filler layer 80 is preferably constituted by a member that has heat dissipation. When the filler layer 80 has heat dissipation, it is possible to improve heat dissipation efficiency because the filler layer 80 receives heat from the backing material layer 54, the FPC 60, the coaxial cables 56, and the like.

The FPC 60 of the ultrasonic vibrator unit 46 has a plurality of electrode pads (not illustrated) electrically connected at one end thereof to the plurality of individual electrodes 52a of the plurality of ultrasonic vibrators 48. The FPC 60 is disposed so as to bend along the side surface in the width direction of the laminated body 47 constituted by the ultrasonic vibrator array 50, the backing material layer 54, and the like. The FPC 60 is also disposed so as to extend beyond the backing material layer 54 on a side opposite to the ultrasonic vibrator array 50 with respect to the backing material layer 54. The portion (portion on the lower side of the backing material layer 54) of the FPC 60 extending beyond the backing material layer 54 on the side opposite to the ultrasonic vibrator array 50 with respect to the backing material layer 54 is a smooth flat surface portion with no bent. In addition, on the lower side of the backing material layer 54, the FPC 60 has the wiring portion 62 that includes the plurality of connection portions 64 wired to the signal wires 56a of the plurality of coaxial cables 56, and the grounded conductive ground portion 66 electrically connected to the vibrator ground 52b of the ultrasonic vibrators 48. Bending and disposing the FPC 60 such that the FPC 60 extends on the lower side of the backing material layer 54, as described above, suppresses the FPC 60 from largely occupying a space inside the distal end portion 40 of the insertion part 22, and therefore, it is possible to perform various wiring by effectively using the space inside the distal end portion 40 while maintaining the size of the distal end portion 40 to be small.

Connection means that uses a solder wire, a conductive paste, or the like or known electrical connection means such as wire bonding may be used as connection means for connecting the individual electrodes 52a of the electrode parts 52 and the electrode pads of the FPC 60 to each other, provided that the means is capable of performing electrical connection.

While only one sheet of the FPC 60 is disposed along the side surface of the laminated body 47 on one side in the width direction, the number of the FPCs 60 to be disposed may be increased, as appropriate when the number of the channels (number of the ultrasonic vibrators 48) of the ultrasonic vibrator array 50 is large. Moreover, the FPC 60 is not necessarily disposed along the side surface of the laminated body 47 in the width direction provided that the FPC 60 electrically connects the electrode parts 52 and the signal wires 56a of the coaxial cables 56 to each other. For example, when the electrode parts 52 are provided on the center side of the laminated body 47 in the width direction, one or more of the FPCs 60 may be embedded and disposed in the backing material layer 54, or the plurality of electrode pads (not illustrated) of the FPC 60 may be disposed so as to face the lower surface of the backing material layer 54.

The heat conductive layer 68 of the ultrasonic vibrator unit 46 is a member for conducting the heat generated in the plurality of ultrasonic vibrators 48 to the ground portion 66 of the FPC 60. In the example illustrated in FIG. 4, the heat conductive layer 68 is integrally formed on one surface of the FPC 60 on the backing material layer 54 side and extends, together with the FPC 60, from the ultrasonic vibrator array 50 along the backing material layer 54 on the lower side of the backing material layer 54. The heat conductive layer 68 is thermally connected to the plurality of ultrasonic vibrators 48 of the ultrasonic vibrator array 50. Consequently, it is possible to provide a heat dissipation path without largely occupying the space inside the distal end portion 40 of the insertion part 22. To efficiently conduct the heat generated in the plurality of ultrasonic vibrators 48, a metal material, such as copper, aluminum, or silver, having high heat conductivity, a highly heat-conductive ceramic, a heat conductive silicone sheet, or the like is preferably used as the heat conductive layer 68. In particular, when the heat conductive layer 68 is constituted by a metal material, it is preferable that the heat conductive layer 68 be removed, as is in the example illustrated in FIG. 4, at a part where the plurality of individual electrodes 52a of the electrode parts 52 and the FPC 60 are connected to each other, to avoid interference between the heat conductive layer 68 and the plurality of individual electrodes 52a. Moreover, the heat conductive layer 68 is preferably in contact with the plurality of ultrasonic vibrators 48 to efficiently conduct the heat generated in the plurality of ultrasonic vibrators 48. Provided that the interference between the plurality of individual electrodes 52a and the heat conductive layer 68 is avoided, the heat conductive layer 68 may be formed by using another configuration, as appropriate.

In the example illustrated in FIG. 4, the heat conductive layer 68 is formed so as to extend to the end portion of the FPC 60 on the side opposite to the ultrasonic vibrator array 50 (on the lower side of the backing material layer 54) and thermally connected, at the end portion on the lower side of the backing material layer 54, to the ground portion 66 disposed on a surface of the FPC 60 on the side opposite to the heat conductive layer 68. In the illustrated example, the heat conductive layer 68 and the ground portion 66 are thermally connected to each other by using a wire (not illustrated) provided inside the FPC 60; however, the heat conductive layer 68 and the ground portion 66 may be thermally connected to each other by using a known member, such as a solder wire or a lead wire, provided that the wire has sufficient heat conductivity. Means for thermally connecting the heat conductive layer 68 and the ground portion 66 is not particularly limited provided that the means has sufficient heat conductivity and does not affect, for example, damage the plurality of ultrasonic vibrators 48 and connection parts thereof as a result of heat. For example, soldering or connection means using silver paste is preferably used. When soldering is used, low melting-point solder is preferably used. The heat conductive layer 68 may be formed so as to extend, through an inner portion of the FPC 60, from the surface on which the heat conductive layer 68 is formed and to be electrically connected to the ground portion 66. When the heat conductive layer 68 is thus disposed on the surface of the FPC 60 on the backing material layer 54 side, the plurality of connection portions 64 of the wiring portion 62 disposed on the surface of the FPC 60 on the side opposite to the backing material layer 54 are suppressed from easily interfering with the heat conductive layer 68. In other words, a wiring structure between the plurality of connection portions 64 and the signal wires 56a of the plurality of coaxial cables 56 is simplified, which improves wiring workability.

In the example illustrated in FIG. 4, the heat conductive layer 68 is provided as a layer of the FPC 60; however, the heat conductive layer 68 may be formed by using means such as coating. When the heat conductive layer 68 is formed by being applied on the surface of the FPC 60, it is possible to use, for example, epoxy adhesive 122-07 manufactured by Creative Materials Inc., thermal grease X-23-8033-1 manufactured by Shin-Etsu Silicone, or the like, as the heat conductive layer 68. In the example illustrated in FIG. 4, the heat conductive layer 68 is disposed on the surface of the FPC 60 on the backing material layer 54 side; however, the heat conductive layer 68 may be provided on the surface of the FPC 60 on the side opposite to the backing material layer 54 and may be provided on both surfaces thereof to improve heat conduction efficiency provided that the heat conductive layer 68 is capable of conducting the heat generated in the plurality of ultrasonic vibrators 48. When the heat conductive layer 68 is disposed on the FPC 60 on the side opposite to the backing material layer 54, the heat conductive layer 68 is preferably formed, for example, on only the backing material layer 54 side of the plurality of connection portions 64 so as to avoid interference between the plurality of connection portions 64 and the heat conductive layer 68.

In the example illustrated in FIG. 4, the heat conductive layer 68 is disposed on only the surface of the FPC 60 on one side on the backing material layer 54 side; however, the heat conductive layer 68 may be disposed on the surface of the FPC 60 on the side opposite to the backing material layer 54 and may be disposed on both surfaces thereof provided that the heat conductive layer 68 is capable of conducting the heat generated in the plurality of ultrasonic vibrators 48 to the ground portion 66. In other words, the heat conductive layer 68 may be arranged on at least one surface of the FPC 60 so as to extend on the lower side of the backing material layer 54.

According to the configuration described above, the heat conductive layer 68 is integrally formed on at least a surface of the FPC 60 on one side and extends along side surfaces of the plurality of ultrasonic vibrators 48 and the backing material layer 54 in the width direction on the lower side of the backing material layer 54. Consequently, it is possible to dissipate the heat generated in the plurality of ultrasonic vibrators 48 to a grounded portion 66 inside the ultrasonic endoscope 12 via the ground portion 66 of the FPC 60 while maintaining the size of the distal end portion 40 of the insertion part 22 to be small. Moreover, since the heat conductive layer 68 is formed on the FPC 60 with no gap therebetween, it is possible to avoid a filling defect of the filler when forming the filler layer 80 so as to fill the gap between the exterior member 41 and the backing material layer 54.

Meanwhile, as described above, the portion where the heat conductive layer 68 is disposed on at least a surface of the FPC 60 on one side is thick compared with the FPC 60 with no heat conductive layer 68 formed, and the portion is not easily bent because the rigidity of the heat conductive layer 68 is added to the portion. Thus, due to the configuration of the distal end portion 40 of the insertion part 22, it may be difficult to, for example, bend and dispose the FPC 60 together with the heat conductive layer 68. Accordingly, for example, by forming the heat conductive layer 68 on only a portion excluding a portion where the FPC 60 is bent, it is possible to easily dispose the FPC 60. In the example illustrated in FIG. 6, the FPC 60 is bent and disposed in contact with and along the side surfaces of the ultrasonic vibrator array 50 and the backing material layer 54 in the width direction. In addition, a heat conductive layer 70 is provided, on the surface of the FPC 60 opposite to the backing material layer 54, only at a portion of the FPC 60 extending on the lower side of the backing material layer 54. In addition, an ultrasonic vibrator unit 69 has a heat conductive member 71 that is thermally connected at one end to the plurality of ultrasonic vibrators 48 of the ultrasonic vibrator array 50 and thermally connected at the other end to the heat conductive layer 70. The heat conductive member 71 is preferably not connected, at the portion where the FPC 60 is bent, to the FPC 60 so as not to hinder the flexibility of the FPC 60. In other words, the heat conductive member 71 is preferably only connected at one end and the other end thereof, respectively, to the plurality of ultrasonic vibrators 48 and the heat conductive layer 70, with no other connected portions. In the example illustrated in FIG. 6, the heat conductive member 71 and a bent portion of the FPC 60 are positioned away from each other, however, may be in contact with each other provided that the heat conductive member 71 and the bent portion of the FPC 60 have no contact point therebetween.

A metal member, such as copper, aluminum, gold, or silver, having high heat conductivity, a heat conductive silicone sheet, or the like is usable as the heat conductive member 71 provided that the heat conductive member 71 is capable of sufficiently conducting the heat generated from the plurality of ultrasonic vibrators 48 to the heat conductive layer 70. A known shape such as a foil shape, a linear shape, a net shape, or the like may be employed as the shape of the heat conductive member 71 provided that the heat conductive member 71 is capable of being easily disposed in addition to having heat conduction efficiency. Moreover, from the point of view of easiness in disposing, the heat conductive member 71 preferably has a length from the plurality of ultrasonic vibrators 48 to the heat conductive layer 70 longer than that of the FPC 60.

When, in particular, the heat conductive member 71 is formed by using a metal, it is preferable that one end of the heat conductive member 71 and the plurality of ultrasonic vibrators 48 be thermally connected to each other such that the heat conductive member 71 and the individual electrodes 52*a* of the electrode parts 52 do not electrically interfere with each other to suppress noise from being included in ultrasonic echo signals (voltage signals). In other words, the heat conductive member 71 is preferably in contact, at a portion excluding the plurality of individual electrodes 52*a*, with the plurality of ultrasonic vibrators 48. When the vibrator ground 52*b* of the electrode parts 52 is grounded, for example, electrically connected to the ground portion 66 or the shield layers 56*c* of the coaxial cables 56, interference between the heat conductive member 71 and the vibrator ground 52*b* is allowable. In addition, means for thermally connecting the heat conductive member 71 to the plurality of ultrasonic vibrators 48 and the heat conductive layer 70 is not particularly limited provided that it is possible to sufficiently conduct the heat from the ultrasonic vibrators 48 to the heat conductive layer 70 and also possible to avoid thermal affection on the ultrasonic vibrators 48, such as damage of the plurality of ultrasonic vibrators 48. As such connection means, known connection means that does not require a high temperature, for example, connection means using low melting-point solder or silver paste is usable.

Figure 6:
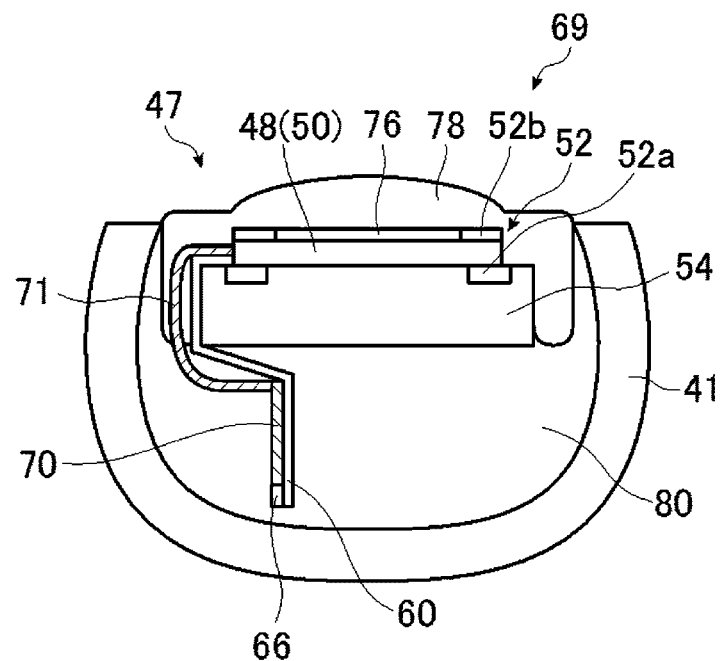
FIG. 6 is a partial cross-sectional view of another example of the ultrasonic vibrator unit illustrated in FIG. 3 and FIG. 4.

In the example illustrated in FIG. 6, a form in which the heat conductive layer 70 is disposed, at the portion extending on the lower side of the backing material layer 54, only on a surface of the FPC 60 on one side is described; however, the heat conductive layer 70 may be disposed on both surfaces of the FPC 60 to, for example, improve heat conduction efficiency.

As a result of forming, as described above, the heat conductive layer 70 at only a flat surface portion of the FPC 60 extending on the lower side of the backing material layer 54 with the heat conductive member 71, which thermally connects the plurality of ultrasonic vibrators 48 and the heat conductive layer 70 to each other, being disposed, at the portion where the FPC 60 is bent along the backing material layer 54, so as to be away from the bent portion of the FPC 60, it is possible to easily dispose the FPC 60 and the heat conductive layer 70 in the ultrasonic vibrator unit 69. In addition, it is possible to reduce gap structures of the ultrasonic vibrator unit 69 by forming the heat conductive layer 70 as a layer of the FPC 60 on the lower side of the backing material layer 54, and it is thus possible to avoid a filling defect of the filler when forming the filler layer 80.

Figure 7:
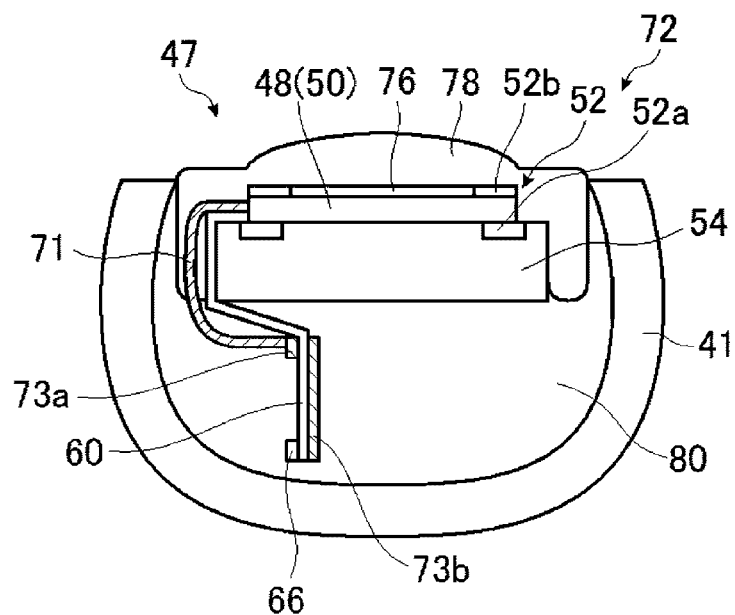
FIG. 7 is a partial cross-sectional view of the other example of the ultrasonic vibrator unit illustrated in FIG. 3 and FIG. 4.

In the example illustrated in FIG. 6, the heat conductive layer 70 is disposed on the surface of the FPC 60 on the side opposite to the backing material layer 54, however, may be disposed also on the surface of the FPC 60 on the backing material layer 54 side. FIG. 7 illustrates another example of the ultrasonic vibrator unit according to the present embodiment. In the example illustrated in FIG. 7, an ultrasonic vibrator unit 72 has a heat conductive layer 73a disposed, at a portion where the FPC 60 extends on the lower side of the backing material layer 54, a portion of the FPC 60 on the side opposite to the backing material layer 54 side; and a heat conductive layer 73b disposed on the surface thereof on the backing material layer 54 side. The heat conductive layers 73a and 73b disposed on both surfaces of the FPC 60 are thermally connected to each other via a wire (not illustrated) provided in the inner portion of the FPC 60. Therefore, the heat conducted from the plurality of ultrasonic vibrators 48 to the heat conductive layer 73a by the heat conductive member 71 is conducted through the wire in the inner portion of the FPC 60. In the example illustrated in FIG. 7, the heat conductive layer 73b on the backing material layer 54 side of the FPC 60 and the ground portion 66 are thermally connected to each other through the FPC 60; however, means for thermally connecting the heat conductive layer 73b and the ground portion 66 is not particularly limited provided that the heat conductive layer 73b and the ground portion 66 are sufficiently thermally connected. For example, a lead wire, a solder wire, or a highly heat-conductive metal member such as a copper foil, or a heat conductive silicone sheet, or the like may be thermally connected by using soldering or known connection means such as silver paste.

Also in FIG. 6 and FIG. 7, similarly to FIG. 4, the view is simplified for description, and the coaxial cables 56 (refer to FIG. 3 and FIG. 5), the wiring portion 62 (refer to FIG. 3), and the connection portions 64 (refer to FIG. 3) are omitted.

In the above configuration, the heat conductive layers 73a and 73b are disposed, at only the portion of the FPC 60 extending on the lower side of the backing material layer 54, on both surfaces of the FPC 60, and the heat conductive layers 73a and 73b are thermally connected to each other via the FPC 60. Thus, the FPC 60 and the heat conductive layers 73a and 73b are easily disposed in the ultrasonic vibrator unit 72, and wiring between the plurality of connection portions 64 of the wiring portion 62 and the signal wires 56a of the coaxial cables 56 is easy, which improves workability in wiring.

The plurality of connection portions 64 of the wiring portion 62 of the FPC 60 are terminals that are electrically connected to the plurality of individual electrodes 52a of the electrode parts 52 electrically connected to the plurality of ultrasonic vibrators 48 via a wire (not illustrated) provided in the inner portion of the FPC 60, and the connection portions 64 are wired to the signal wires 56a of the plurality of coaxial cables 56. In the example illustrated in FIG. 4, the plurality of connection portions 64 are disposed on the same surface of the FPC 60 as the surface on which the ground portion 66 is disposed, so as to be on the backing material layer 54 side of the ground portion 66. Needless to say, a location where the plurality of connection portions 64 are disposed is not particularly limited. The connection portions 64 may be disposed at an arbitrary location as appropriate to, for example, improve wiring workability. In addition, the total number of the plurality of connection portions 64 is preferably at least equal to the number of the channels of the ultrasonic vibrator array 50. Thus, the plurality of connection portions 64 may be arranged in multiple rows on the FPC 60, as necessary.

In the example illustrated in FIG. 3 and FIG. 4, the ground portion 66 of the FPC 60 is a conductive electrode that is electrically connected to the vibrator ground 52b of the electrode parts 52 via a wire (not illustrated) inside the FPC 60, and the ground portion 66 is electrically connected to the shield layers 56c of the plurality of coaxial cables 56. Thus, it is possible to cause the shield layers 56c of the plurality of coaxial cables 56 electrically connected to the ground portion 66 to have the same ground potential. The ground portion 66 is thermally connected to the heat conductive layer 68 disposed on one of the surfaces of the FPC 60. It is possible to dissipate, by using a simple structure, the heat generated in the plurality of ultrasonic vibrators 48 by thermally connecting the heat conductive layer 68 and the ground portion 66 to each other as described above. In example illustrated in FIGS. 3, 4, 6 and 7, the ground portion 66 is disposed, at an end portion of the FPC 60 on the lower side of the backing material layer 54, on the surface of the FPC 60 on the side opposite to the backing material layer 54; however, the position at which the ground portion 66 is disposed may be changed, as appropriate, in accordance with the configuration of the distal end portion 40 of the insertion part 22, the configuration of the wiring, and the like. For example, the ground portion 66 may be disposed on the surface of the FPC 60 on the backing material layer 54 side and on the portion of the FPC 60 extending on the lower side of the backing material layer 54 on the backing material layer 54 side.

The ground portion 66 has a heat dissipation effect, even when the ground portion 66 is not grounded, for example, when the shield layers 56c of the plurality of coaxial cables 56 connected to the ground portion 66 are not grounded, because the ground portion 66 conducts the heat from the plurality of ultrasonic vibrators 48 to a member that has a heat capacity larger than that of the heat conductive layer 68 and the ground portion 66. When the ground portion 66 is grounded and, in particular, when the heat conductive layer 68 is formed of a metal, the heat conductive layer 68 does not interfere with ultrasonic echo signals (voltage signals) of the plurality of ultrasonic vibrators 48, and it is thus possible to suppress noise from outside from being included in ultrasonic echo signals.

Meanwhile, for example, when the heat conductive layer 68 is disposed on the same surface of the FPC 60 as the surface on which the wiring portion 62 is disposed in the example illustrated in FIG. 4, wiring is complicated because the plurality of coaxial cables 56, the respective signal wires 56a of which are wired to the plurality of connection portions 64, and the wiring between the heat conductive layer 68 and the ground portion 66 are present on the same surface. Thus, the heat conductive layer 68 is disposed on the surface of the FPC 60 so as to suppress the plurality of connection portions 64 from interfering with the heat conductive layer 68 and the ground portion 66, thereby simplifying the wiring structure. In the example illustrated in FIG. 8, the ground portion 66 of the FPC 60 is disposed on one end side of the FPC 60, and the plurality of connection portions 64 are disposed adjacent to the ground portion 66. A heat conductive layer 74 disposed on the same surface of the FPC 60 as the surface on which the wiring portion 62 is disposed is formed at a portion excluding the plurality of connection portions 64 so as to surround the plurality of connection portions 64 and so as to be thermally connected to the ground portion 66. Since the heat conductive layer 74 is thus formed so as not to interfere with the plurality of connection portions 64 and so as to be connected to the ground portion 66, the heat conductive layer 74 and the ground portion 66 do not need to be connected to each other by using soldering or connection means using silver paste, which suppresses the plurality of wires of the wiring portion 62 from being complicated. Consequently, it is possible to improve wiring workability of the wiring portion 62 and also possible to reduce possibility of disconnection of the wiring portion 62.

Figure 8:
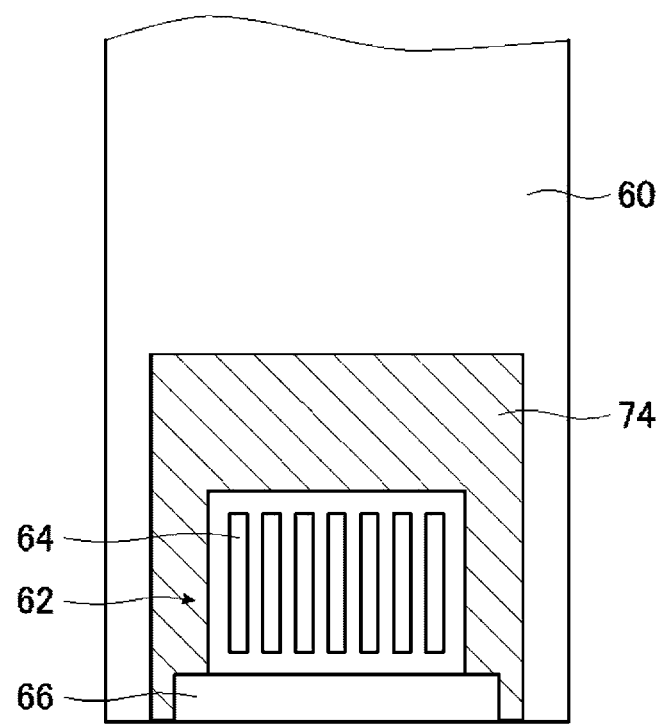
FIG. 8 is a schematic partially enlarged view of another example of a configuration of a wiring portion and a ground portion of a flexible printed wiring board and a heat conductive layer of the ultrasonic unit illustrated in FIGS. 3 to 7.

FIG. 8 is a schematic view simplified for describing the configuration of the heat conductive layer 74. When the heat conductive layer 74 is disposed on only the same surface of the FPC 60 as the surface on which the wiring portion 62 is disposed, the heat conductive layer 74 may be formed, at a portion excluding the plurality of connection portions 64, at least on one entire surface of the portion extending on the lower side of the backing material layer 54.

The configuration of the distal end portion 40 of the insertion part 22 of the ultrasonic endoscope 12 according to the present embodiment presented above enables the heat generated from the plurality of ultrasonic vibrators 48 constituting the ultrasonic vibrator array 50 to be conducted to the heat conductive layer 68, 70, 73a, 73b, or 74 and dissipated via the ground portion 66 to the grounded portion, such as the shield layers 56c of the coaxial cables 56, inside the ultrasonic endoscope 12. In addition, since the heat conductive layer 68, 70, 73a, 73b, or 74 is formed so as not to interfere with the plurality of connection portions 64 of the wiring portion 62 connected to the signal wires 56a of the plurality of coaxial cables 56, it is possible to suppress noise received from outside from being included in ultrasonic echoes. Moreover, each of the heat dissipation structures described above is simple and does not occupy a large space in the distal end portion 40 of the ultrasonic endoscope 12. Thus, it is possible to efficiently perform heat dissipation while maintaining the size of the distal end portion 40 of the insertion part 22 to be small. In the present embodiment, a heat dissipation structure of the ultrasonic endoscope 12 of a convex type has been described; however, the above heat dissipation structure does not depend on the shape of the ultrasonic endoscope and is applicable, as a matter of course, also to an ultrasonic endoscope that has another shape such as a radial shape.

The endoscopic observation portion 38 is constituted by an observation window 82, an objective lens 84, a solid-state imaging element 86, illumination windows 88, a cleaning nozzle 90, a wiring cable 92 formed of a plurality of coaxial cables (not illustrated), and the like.

The observation window 82 is attached so as to face obliquely above the distal end portion 40. Light that has entered the observation window 82 and is reflected by the observation target part is formed into an image on an imaging surface of the solid-state imaging element 86 by the objective lens 84. The solid-state imaging element 86 outputs a captured signal by photoelectrically converting the reflected light, which has been transmitted through the observation window 82 and the objective lens 84 and formed into the image on the imaging surface, of the observation target part. Examples of the solid-state imaging element 86 are a CCD (charge coupled device) and a CMOS (complementary metal oxide semiconductor). The captured image signal output by the solid-state imaging element 86 is transmitted to the endoscope processor 16 through the universal cord 26, via the wiring cable 92 extending from the insertion part 22 to the operating part 24. The endoscope processor 16 performs various types of signal processing and image processing on the transmitted captured signal and displays the captured signal as an endoscopic optical image on the monitor 20.

The illumination windows 88 are provided on both sides of the observation window 82 with the observation window therebetween. An exit end of the light guide (not illustrated) is connected to the illumination windows 88. The light guide extends from the insertion part 22 to the operating part 24, and the incident end thereof is connected to the light source device 18 connected via the universal cord 26. The illumination light emitted by the light source device 18 is transmitted through the light guide and emitted from the illumination windows 88 onto an observation target portion.

The cleaning nozzle 90 spouts out air or cleaning water from the water supply tank 21a via the air-water supply pipe line inside the ultrasonic endoscope 12 toward the observation window 82 and the illumination windows 88 to clean surfaces of the observation window 82 and the illumination windows 88.

The distal end portion 40 is provided with the treatment tool lead-out port 44. The treatment tool lead-out port 44 is connected to a treatment tool channel 45 inserted into an inner portion of the insertion part 22. A treatment tool inserted into the treatment tool insertion port 30 is led into a body cavity through the treatment tool lead-out port 44 via a treatment tool channel 45. The treatment tool lead-out port 44 is positioned between the ultrasonic observation portion 36 and the endoscopic observation portion 38. However, when it is configured such that the movement of a treatment tool led into a body cavity through the treatment tool lead-out port 44 is checked in an ultrasound image, the treatment tool lead-out port 44 is preferably disposed close to the ultrasonic observation portion 36.

In an inner portion of the treatment tool lead-out port 44, while no illustration is provided, an erecting base that varies a lead-out direction of a treatment tool led into a body cavity through the treatment tool lead-out port 44 may be provided. A wire (not illustrated) is attached to the erecting base. The erecting angle of the erecting base is varied by using, as means, pushing-pulling operation using an erecting lever (not illustrated) of the operating part 24 to cause a treatment tool to be lad out in a desired direction.

To observe an inner portion of a body cavity by using the ultrasonic endoscope 12, the insertion part 22 is first inserted into the body cavity to search for an observation target part while observing, on the monitor 20, an endoscopic optical image acquired by the endoscopic observation portion 38.

Next, when the distal end portion 40 reaches the observation target part, and an instruction to acquire an ultrasonic tomographic image is issued, a drive control signal is input to the ultrasonic vibrators 48 from the ultrasonic processor 14 via the plurality of coaxial cables 56, the FPC 60, and the electrode parts 52 included in the ultrasonic endoscope 12. When the drive control signal is input, a prescribed voltage is applied to both electrodes of the ultrasonic vibrators 48. Then, the piezoelectric bodies of the ultrasonic vibrators 48 are excited to emit ultrasonic waves toward the observation target part through the acoustic lens 78.

After the ultrasonic waves are emitted, echo signals from the observation target part are received by the ultrasonic vibrators 48. The emission of the ultrasonic waves and the reception of the echo signals are repeatedly performed while shifting the driven ultrasonic vibrators 48 by using an electronic switch such as a multiplexer. The observation target part is thereby scanned with the ultrasonic waves. In the ultrasonic processor 14, an ultrasonic tomographic image is generated on the basis of a detection signal output from the ultrasonic vibrators 48 when the echo signals are received. The generated ultrasonic tomographic image is displayed on the monitor 20.

Second Embodiment

Figure 9:
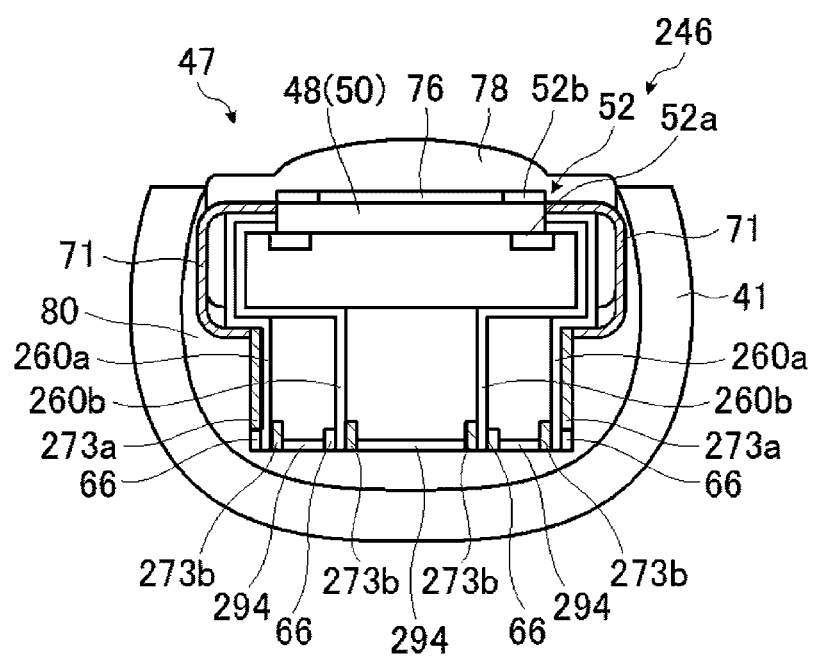
FIG. 9 is a partial cross-sectional view of an example of the ultrasonic vibrator unit of the ultrasonic observation portion in a second embodiment of the present invention.

In the first embodiment illustrated in FIGS. 1 to 8, the ultrasonic vibrator unit in which one sheet of the FPC is disposed is mainly described; however, a plurality of the FPCs may be disposed in accordance with the number of the channels of the ultrasonic vibrator array. FIG. 9 illustrates a partial cross-sectional view of an ultrasonic vibrator unit of an ultrasonic observation portion in a second embodiment of the present invention. FIG. 9 is simplified for description, similarly to FIGS. 4, 6, and 7 of the first embodiment, and the plurality of connection portions (not illustrated) of the wiring portion 62 and the plurality of coaxial cables (not illustrated) wired to the plurality of connection portions are omitted. Compared with the ultrasonic vibrator unit 69 according to the first embodiment illustrated in FIG. 6, an ultrasonic vibrator unit 246 according to the second embodiment illustrated in FIG. 9 only differs from the ultrasonic vibrator unit 69 in terms of having, on both side-surface sides of a laminated body 47, FPCs 260a that each include heat conductive layers 273a and 273b thermally connected to the heat conductive member 71 that is further thermally connected to the plurality of ultrasonic vibrators 48; FPCs 260b between a pair of the FPCs 260a and 260a, each FPC 260b including a heat conductive layer 273b; and second heat conductive members 294 that thermally connect the heat conductive layers 273a and 273b of the plurality of FPCs 260a and 260b to each other. In terms of other features, the ultrasonic vibrator unit 246 has the same configuration as the configuration of the ultrasonic vibrator unit 69; therefore, the same elements are given the same reference signs, and detailed description thereof will be omitted.

In the example illustrated in FIG. 9, the ultrasonic vibrator unit 246 has the pair of FPCs (outside FPCs) 260a and 260a disposed on the outermost side with respect to a center side of the backing material layer 54; the FPCs (inside FPCs) 260b and 260b disposed between the pair of FPCs 260a and 260a; and the second heat conductive members 294 that thermally connect the four FPCs 260a, 260a, 260b, and 260b to each other. Regarding the pair of outside FPCs 260a, similarly to the example according to the first embodiment illustrated in FIG. 6, the heat conductive layers 273a are disposed on surfaces (outside surfaces) of the FPCs 260a on the side opposite to the backing material layer 54, and the heat conductive layers 273a and the plurality of ultrasonic vibrators 48 are thermally connected to each other via the heat conductive members (first heat conductive members) 71. The heat conductive layers 273b are disposed on surfaces (inside surfaces) of the plurality of FPCs 260a and 260b on the backing material layer 54 side, and the heat conductive layers 273b and the ground portions 66 of the FPCs 260a and 260b adjacent to each other and the FPCs 260b and 260b adjacent to each other are thermally connected to each other via the second heat conductive members 294.

FIG. 9 is simplified for description, and wiring portions (not illustrated) disposed at the FPCs 260a and 260b, a plurality of connection portions (not illustrated), and coaxial cables (not illustrated) connected to the wiring portions and the ground portions 66 are omitted.

The plurality of outside FPCs 260a of the ultrasonic vibrator unit 246 are each electrically connected, at one end, to a plurality of individual electrodes 52a of electrode parts 52 disposed on end surface sides of the ultrasonic vibrator array 50 in the width direction. The outside FPCs 260a are disposed so as to bend along side surfaces of the plurality of ultrasonic vibrators 48 and the backing material layer 54 and so as to extend on the lower side of the backing material layer 54. In the illustrated example, the outside FPCs 260a each have the heat conductive layer 273a extending on the lower side of the backing material layer 54, the heat conductive layer 273a being disposed on the outside surface at a smooth flat surface portion; the ground portion 66 that is provided on the outside surface of an end portion (lower end portion) of the flat surface portion of the FPC 260a on the side opposite to the backing material layer 54, the ground portion 66 being electrically connected to shield layers (not illustrated) of the plurality of coaxial cables (not illustrated); wiring portions (not illustrated) that are provided on the outside surfaces of the FPC 260a, the wiring portions being constituted by the plurality of connection portions (not illustrated) electrically connected to signal wires (not illustrated) of the plurality of coaxial cables; and the inside FPC 260b that is thermally connected to the ground portion 66 via a wire (not illustrated) provided inside the FPC 260a. Since the heat conductive layers 273a are thermally connected to the plurality of ultrasonic vibrators 48 through the heat conductive members 71, the heat generated in the plurality of ultrasonic vibrators 48 is dissipated to the shield layers of the plurality of coaxial cables via the ground portions 66 connected to the heat conductive layers 273a.

In the illustrated example, the pair of FPCs 260a are disposed on both side surfaces of the laminated body 47 in the width direction; however, the FPC 260a may be disposed on only one of both side surface sides of the laminated body 47 in the width direction in accordance with the number of the channels of the ultrasonic vibrator array 50. In the illustrated example, the heat conductive layers 273a thermally connected to the plurality of ultrasonic vibrators 48 are disposed on the outside surfaces of the FPCs 260a; however, the heat conductive layers 273b thermally connected to the plurality of ultrasonic vibrators 48 may be disposed on the inside surfaces of the FPCs 260a. The heat conductive layers 273a and 273b thermally connected to the plurality of ultrasonic vibrators 48 may be disposed on both surfaces of the FPCs 260a. The FPCs 260a are not necessarily disposed along the side surfaces of the laminated body 47 in the width direction provided that the FPCs 260a are electrically connected to the plurality of individual electrodes 52a of the electrode parts 52. For example, when the plurality of individual electrodes 52a are disposed on the center side of the backing material layer 54 in the width direction, the plurality of FPCs 260a and 260b may be disposed so as to be on the lower side of the backing material layer 54 or such that portions thereof are buried in the backing material layer 54 by, for example, electrically connecting wires that are extended through the backing material layer 54 to the lower side thereof and that are electrically connected to the plurality of individual electrodes 52a to the FPCs 260a and 260b corresponding thereto.

Similarly to the outside FPCs 260a, the inside FPCs 260b of the ultrasonic vibrator unit 246 are electrically connected, at one end, to the plurality of individual electrodes 52a of the electrode parts 52 disposed on the end surface sides of the ultrasonic vibrator array 50 in the width direction. The inside FPCs 260b are disposed so as to bend along the side surfaces of the plurality of ultrasonic vibrators 48 and the backing material layer 54 and so as to extend on the lower side of the backing material layer 54. In the example illustrated in FIG. 9, the inside FPCs 260b have the same configuration as that of the outside FPCs 260a except for a feature in which the heat conductive layers 273a are not disposed on the outside surfaces. The inside FPCs 260b each have the ground portion 66 that is provided on the outside surface of the lower end portion of the flat surface portion of the FPC 260a, the ground portion 66 being electrically connected to the shield layers (not illustrated) of the plurality of coaxial cables (not illustrated); the wiring portions (not illustrated) that are provided on the outside surface of the FPC 260*b* and constituted by a plurality of connection portions (not illustrated) electrically connected to the signal wires (not illustrated) of the plurality of coaxial cables; and the heat conductive layer 273*b* that is thermally connected to the ground portion 66 via a wire (not illustrated) provided inside the FPC 260*b*. The ground portions 66 of the inside FPCs 260*b* are thermally connected, via the second heat conductive members 294, to the heat conductive layers 273*b* disposed on the inside surfaces of the adjacent outside FPCs 260*a*. Further, the heat conductive layers 273*b* of the inside FPCs 260*b* are thermally connected, via the second heat conductive members 294, to the heat conductive layers 273*b* of the adjacent inside FPCs 260*b*.

In the illustrated example, similarly to the outside FPCs 260*a*, the pair of FPCs 260*b* are disposed on both side surfaces of the laminated body 47 in the width direction; however, the FPC 260*a* may be disposed only on one of side surfaces of the laminated body 47 in the width direction and the number of the disposed inside FPCs 260*b* may be increased in accordance with the number of the channels of the ultrasonic vibrator array 50. In the illustrated example, the heat conductive layers 273*a* and 273*b* thermally connected to the plurality of ultrasonic vibrators 48 are not disposed on the FPCs 260*b*; however, the heat conductive layers 273*a* and 273*b* thermally connected to the plurality of ultrasonic vibrators 48 may be disposed on the outside surface, the inside surface, or both surfaces of the FPCs 260*b*. In this case, it is possible to dissipate the heat of the plurality of ultrasonic vibrators 48 to the shield layers of the plurality of coaxial cables via the ground portions 66 and the second heat conductive members 294 of the inside FPCs 260*b*, and therefore, the heat conductive layers 273*a* or 273*b* thermally connected to the plurality of ultrasonic vibrators 48 is not necessarily disposed on the outside FPCs 260*a*. Moreover, similarly to the above-described outside FPCs 260*a*, the inside FPCs 260*b* is not necessarily disposed along the side surfaces of the laminated body 47 in the width direction provided that the inside FPCs 260*b* are electrically connected to the plurality of individual electrodes 52*a* of the electrode parts 52.

In the example illustrated in FIG. 9, the heat conductive layers 273*a* of the ultrasonic vibrator unit 246 are disposed on the outside surfaces of the outside FPCs 260*a* at portions extending on the lower side of the backing material layer 54, and the heat conductive layers 273*a* are thermally connected, at one end on the backing material layer 54 side, to the heat conductive members 71 and, at the other end, to the ground portions 66 of the FPCs 260*a*. The heat conductive layers 273*b* of the ultrasonic vibrator unit 246 are disposed on at least portions of the inside surfaces of the FPCs 260*a* and 260*b*, at portions extending on the inner circumferential side of the backing material layer 54. In the example illustrated in FIG. 9, the heat conductive layers 273*b* and 273*b* of the pair of outside FPCs 260*a* and 260*a* are thermally connected to the ground portions 66 disposed on the surfaces on the opposite side via wires (not illustrated) provided inside the outside FPCs 260*a*. The heat conductive layers 273*b* disposed on the inside surfaces of the inside FPCs 260*b* are thermally connected, via wires inside the inside FPCs 260*b*, to the ground portions 66 disposed on surfaces of the FPCs 260*b* on the side opposite to the heat conductive layers 273*b*.

The locations where the heat conductive layers 273*a* and 273*b* are formed are not limited to the example illustrated in FIG. 9 provided that it is possible to conduct the heat generated in the plurality of ultrasonic vibrators 48 to the ground portions 66. For example, similarly to the first embodiment illustrated in FIG. 7, the heat conductive layers 273*b* disposed on the inside surfaces of the FPCs 260*a* and the FPCs 260*b* may be disposed on the entire surfaces on one side, and the heat conductive layers 273*a* disposed on the outside surfaces of the FPCs 260*a* and the FPCs 260*b* may be formed, for the thermal connection to the heat conductive members 71, at portions of the outside surfaces. Moreover, the heat conductive layers 273*a* or 273*b* may be disposed on the entire surface on one side or both sides of the plurality of FPCs 260*a* and 260*b* without providing the heat conductive members 71, as illustrated in FIG. 4 of the first embodiment.

The second heat conductive members 294 of the ultrasonic vibrator unit 246 are for thermally connecting the plurality of heat conductive layers 273*a* and 273*b* disposed on the plurality of FPCs 260*a* or 260*b* to each other. Thus, it is possible to sufficiently dissipate the heat generated in the plurality of ultrasonic vibrators 48, via the respective ground portions 66, to the shield layers of all of the coaxial cables connected to the plurality of FPCs 260*a* and 260*b*. The second heat conductive members 294 preferably have high heat conductivity, and a metal such as copper, brass, aluminum, gold, or silver, a heat conductive silicone, or a highly heat-conductive ceramic is usable as the second heat conductive members 294. The shape of the second heat conductive members 294 is not particularly limited provided that heat conduction is not impeded. A shape such as a linear shape, a foil shape, a net shape, or a shape with which the second heat conductive members 294 are easily connected, like a pin, to the ground portions 66 and the heat conductive layers 273*b* of the FPCs 260*a* or 260*b* is usable, as appropriate, as the shape of the second heat conductive members 294.

The second heat conductive members 294 need only to be capable of thermally connecting the ground portions 66 of the plurality of FPCs 260*a* and 260*b* to each other, and therefore, the second heat conductive members 294 may thermally connect the ground portions 66 of the plurality of FPCs 260*a* and 260*b* to each other in a manner other than via the heat conductive layers 273*b*.

Similarly to the ground portions 66 according to the first embodiment illustrated in FIGS. 3 and 4 and FIGS. 6 to 8, the ground portions 66 of the FPCs 260*a* and 260*b* illustrated in FIG. 9 are conductive members that are electrically connected to the shield layers (not illustrated) of the plurality of coaxial cables (not illustrated). Thus, it is possible to dissipate, to the shield layers of the plurality of coaxial cables, heat that is conducted via the heat conductive members 71 thermally connected to the plurality of ultrasonic vibrators 48, the heat conductive layer 273*a* or 273*b* disposed on the FPCs 260*a* and 260*b*, and the second heat conductive members 294. In the illustrated example, the ground portions 66 are provided on the outside surfaces of the FPCs 260*a* and 260*b*; however, the ground portions 66 may be provided on the inside surfaces of the FPCs 260*a* and 260*b* provided that the ground portions 66 are thermally connected to the heat conductive layers 273*a* and 273*b* and the shield layers of the plurality of coaxial cables and does not impair workability in wiring to the plurality of shield layers. Moreover, the arrangement of the ground portions 66 is not particularly limited to the locations illustrated in FIG. 9 provided that the ground portions 66 are disposed on the FPCs 260*a* and 260*b*.

As described above, according to the second embodiment illustrated in FIG. 9, when the plurality of FPCs 260*a* and 260*b* are disposed in the ultrasonic vibrator unit 246, it is possible to thermally connect the ground portions 66 and the heat conductive layers 273*b* of the adjacent FPCs 260*a* and 260*b* to each other and the heat conductive layers 273*b* of the adjacent FPCs 260*b* to each other. Therefore, it is possible to sufficiently dissipate the heat generated in the plurality of ultrasonic vibrators 48 to the shield members of the plurality of coaxial cables via the heat conductive members 71, the heat conductive layers 273*a* and 273*b*, the second heat conductive members 294, and the ground portions 66.

Similarly to the first embodiment, also in the present embodiment, a heat dissipation structure of the ultrasonic endoscope of a convex type has been described; however, the above heat dissipation structure does not depend on the shape of the ultrasonic endoscope and is applicable, as a matter of course, also to an ultrasonic endoscope that has another shape such as a radial shape.

Third Embodiment

In the above description, the heat dissipation structure according to the present invention applied to an ultrasonic endoscope of a convex type has been mainly described; however, the heat dissipation structure according to the present invention is applicable also to an ultrasonic endoscope that has an ultrasonic observation portion of other types other than the convex type, for example, a radial type. In the present embodiment, a heat dissipation structure of a radial-type ultrasonic observation portion will be described. An ultrasonic endoscope 312 according to the present embodiment illustrated in FIGS. 10 and 11 only differs from the ultrasonic endoscope 12 according to the first embodiment illustrated in FIGS. 1 to 3 in terms of having a distal end portion 340 that includes a radial-type ultrasonic observation portion 336 and an endoscopic observation portion 338, instead of including the distal end portion 40 that includes the convex-type ultrasonic observation portion 36 and the endoscopic observation portion 38, and in terms of other features, the ultrasonic endoscope 312 has the same configuration as that of the ultrasonic endoscope 12. In the radial-type ultrasonic observation portion 336, in particular, members that are same as the coaxial cables 56 and the outer sheath 58 according to the first embodiment illustrated in FIGS. 3 and 5 are used. Therefore, in FIGS. 10 and 11, the coaxial cables 56 and the outer sheath 58 are given the same reference signs as those in FIGS. 3 and 5, and detailed description thereof will be omitted.

Figure 10:
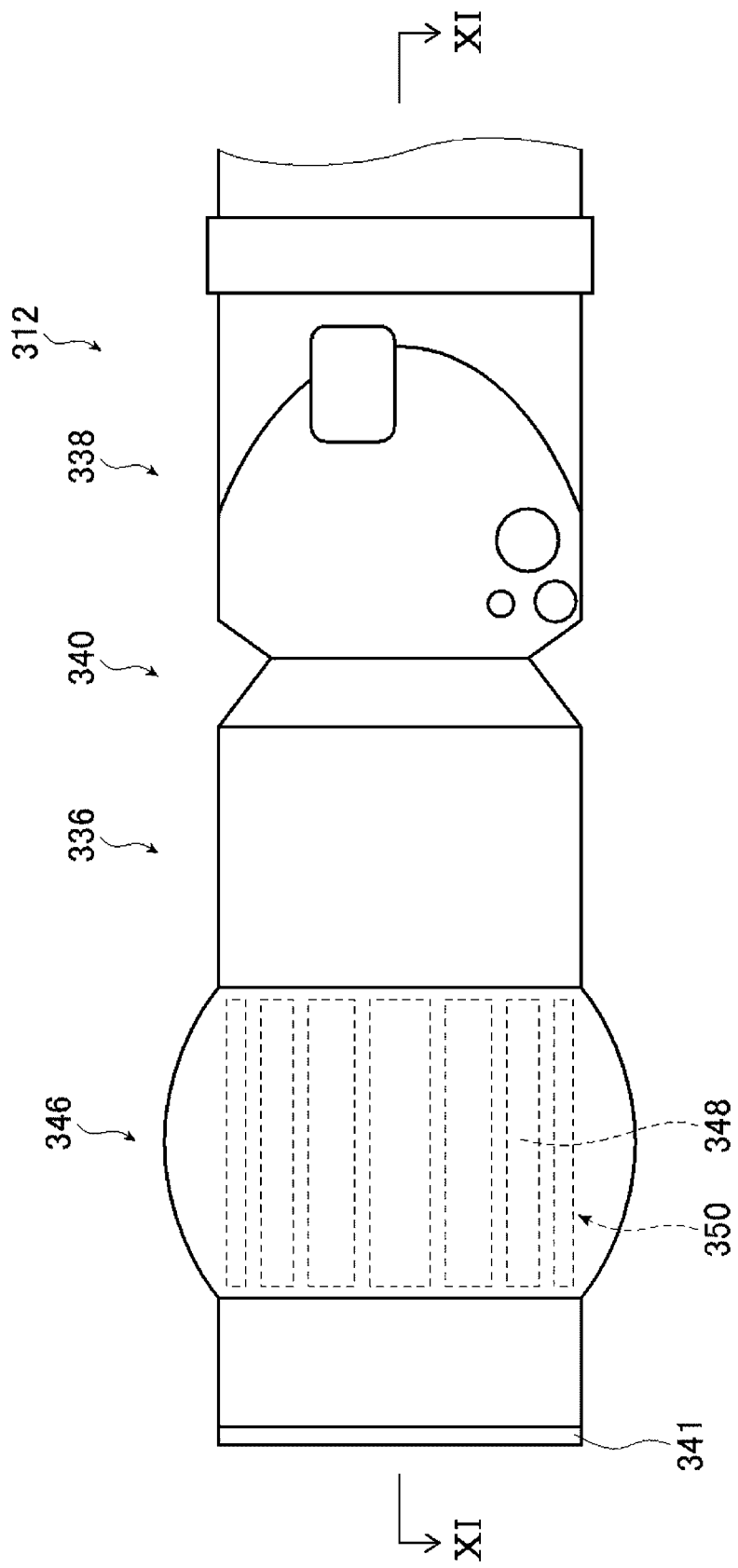
FIG. 10 is a partially enlarged plan view of the distal end portion of the ultrasonic endoscope in a third embodiment of the present invention.
Figure 11:
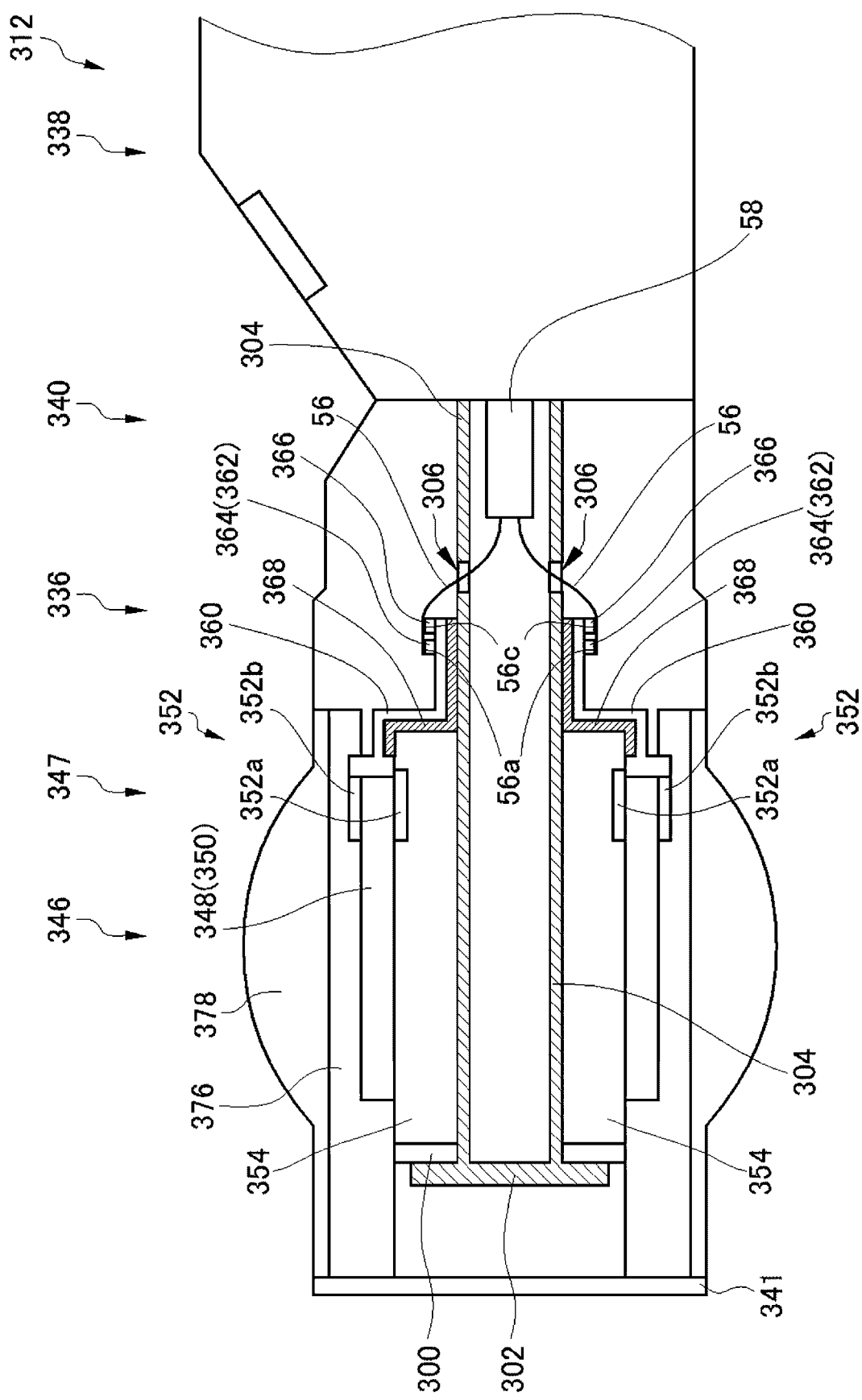
FIG. 11 is a view in the arrow direction of line XI-XI illustrated in FIG. 10, which is a partial longitudinal sectional view of the distal end portion of the ultrasonic endoscope illustrated in FIG. 10.
Figure 12:
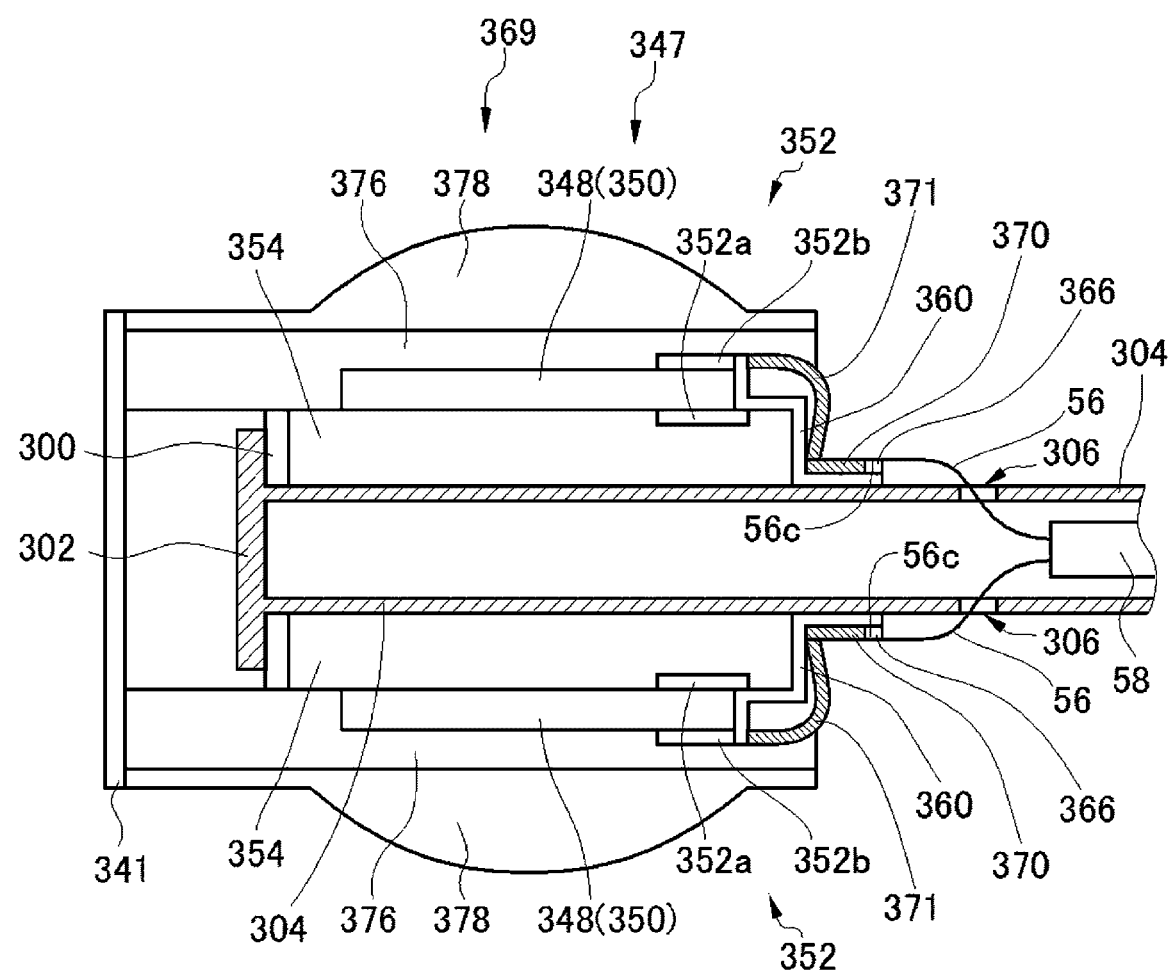
FIG. 12 is a partial longitudinal sectional view of another example of the ultrasonic vibrator unit illustrated in FIG. 11.

FIG. 10 is a partially enlarged plan view illustrating a distal end portion of an insertion part of an ultrasonic endoscope according to the present embodiment. FIG. 11 is a view in the arrow direction of line XI-XI illustrated in FIG. 10, which is a partial longitudinal sectional view of the distal end portion of the insertion part of the ultrasonic endoscope illustrated in FIG. 10. FIG. 12 is a schematic partial longitudinal sectional view of the distal end portion of the insertion part of the ultrasonic endoscope illustrated in FIGS. 10 and 11.

As illustrated in FIGS. 10 and 11, the ultrasonic endoscope 312 according to the present embodiment is a radial-type ultrasonic endoscope in which the ultrasonic observation portion 336 of the distal end portion 340 has an ultrasonic vibrator unit 346 that includes an ultrasonic vibrator array 350 in which a plurality of ultrasonic vibrators 348 are arrayed in a cylindrical shape. In the example illustrated in FIGS. 10 and 11, the ultrasonic observation portion 336 is disposed closer than the endoscopic observation portion 338 to a distal end side of the ultrasonic endoscope 312.

The ultrasonic endoscope 312 according to the present invention may include a mechanism that leads out treatment tools such as forceps, a puncture needle, and a high-frequency knife, similarly to the ultrasonic endoscope 12 according to the first embodiment illustrated in FIGS. 1 to 3. A treatment tool lead-out port (not illustrated) through which these treatment tools are led out may be present closer than the plurality of ultrasonic vibrators 348 to the distal end side of the ultrasonic endoscope 312 or may be present on a proximal end side thereof.

The endoscopic observation portion 338 of the ultrasonic endoscope 312 according to the present embodiment has the same configuration as that of the endoscopic observation portion 38 of the ultrasonic endoscope 12 according to the first embodiment illustrated in FIGS. 2 and 3, and, as a matter of course, the endoscopic observation portion 338 has an observation window (82), an objective lens (84), a solid-state imaging element (86), illumination windows (88), a cleaning nozzle (90), a wiring cable (92), and the like.

As illustrated in FIGS. 10 and 11, the ultrasonic observation portion 336 according to the present embodiment is constituted by the ultrasonic vibrator unit 346, an exterior member 341 to which the ultrasonic vibrator unit 346 is attached to be held, and the plurality of coaxial cables 56 wired to the ultrasonic vibrator unit 346.

In the example illustrated in FIG. 11, the ultrasonic vibrator unit 346 has the ultrasonic vibrator array 350 in which the plurality of ultrasonic vibrators 348 are arrayed in the cylindrical shape; electrode parts 352 electrically connected to the ultrasonic vibrator array 350; a backing material layer 354 that supports, from a side of a surface (inside surface of the ultrasonic vibrators 348) on a center side of the ultrasonic vibrator unit 346, each ultrasonic vibrator 348 of the ultrasonic vibrator array 350; an acoustic matching layer 376 laminated on the side opposite (outer side of the ultrasonic vibrator array 350) to the backing material layer 354 with respect to the ultrasonic vibrator array 350; and an acoustic lens 378 laminated on the side opposite (outer side of the acoustic matching layer 376) to the ultrasonic vibrator array 350 with respect to the acoustic matching layer 376. As described above, the ultrasonic vibrator unit 346 has a laminated body 347 formed of the acoustic lens 378, the acoustic matching layer 376, the ultrasonic vibrator array 350, and the backing material layer 354.

The ultrasonic vibrators 348, the ultrasonic vibrator array 350, the electrode parts 352, the backing material layer 354, the acoustic matching layer 376, the acoustic lens 378, and the laminated body 347 according to the present embodiment respectively differ from the ultrasonic vibrators 48, the ultrasonic vibrator array 50, the electrode parts 52, the backing material layer 54, the acoustic matching layer 76, the acoustic lens 78, and the laminated body 47 according to the first embodiment illustrated in FIGS. 2 to 4 in terms of shape but are identical thereto in terms of configurations and functions thereof; therefore, description thereof will be omitted.

In addition, the ultrasonic vibrator unit 346 has a FPC 360 that is disposed in contact with each of a surface of the acoustic matching layer 376 on a side opposite to the acoustic lens 378, a side surface of the ultrasonic vibrator array 350 in the width direction, and the backing material layer 354 and that is electrically connected to the electrode parts 352; a heat conductive layer 368 provided on a surface of the FPC 360 on the backing material layer 354 side; an annular plate 300 for fixing a position of a cylindrical member 304, which will be described later, the annular plate 300 being an annular plate material that is disposed such that a side surface in the width direction on the side opposite (proximal end side of the ultrasonic endoscope 312) to the distal end side of the ultrasonic endoscope 312 is in contact with a side surface of the backing material layer 354 on the distal end side of the ultrasonic endoscope 312; a support plate 302 that is joined to a surface of the annular plate 300 on the side opposite to the backing material layer 354, the support plate 302 being a disc-shaped plate material having an outer diameter larger than the inner diameter of the annular plate 300; and the cylindrical member 304 for supporting the laminated body 347, the cylindrical member 304 being in contact with a surface of the backing material layer 354 on the side opposite (inner side of the backing material layer 354) to the ultrasonic vibrator array 350 and being in contact with and joined to the support plate 302 at an end surface on the distal end side of the ultrasonic endoscope 312.

The electrode parts 352 of the ultrasonic vibrator unit 346 has individual electrodes 352a for transmitting and receiving voltage signals such as driving signals and ultrasonic echo signals to or from each of the plurality of ultrasonic vibrators 348; and a vibrator ground 352b as a grounding electrode of the plurality of ultrasonic vibrators 348. In the example illustrated in FIG. 11, the individual electrodes 352a are disposed on the inner side of the ultrasonic vibrators 348 at an end portion on the proximal end side of the ultrasonic endoscope 312 and electrically connected to a plurality of electrode pads (not illustrated) of the FPC 360. The vibrator ground 352b is disposed on the outer side of the ultrasonic vibrators 348 at an end portion on the proximal end side of the ultrasonic endoscope 312 and electrically connected to an electrode pad different from the electrode pads of the FPC 360 electrically connected to the individual electrodes 352a. As described later, the plurality of electrode pads electrically connected to the plurality of individual electrodes 352a are electrically connected to the signal wires 56a of the plurality of coaxial cables 56, and the electrode pad electrically connected to the vibrator ground 352b is electrically connected to the shield layers 56c of the coaxial cables 56. Thus, the individual electrodes 352a and the vibrator ground 352b are electrically connected to the signal wires 56a of the coaxial cables 56 and the shield layers 56c of the coaxial cables 56, respectively.

Since the vibrator ground 352b is a grounding electrode for the plurality of ultrasonic vibrators 348, it is preferable that respective ground potentials thereof be the same potential. Therefore, the vibrator ground 352b is preferably a common electrode of the plurality of ultrasonic vibrators 348. In addition, the vibrator ground 352b needs only to be electrically connected to a grounded portion and is not necessarily connected via the electrode pad (not illustrated) of the FPC 360 and not necessarily electrically connected to the shield layers 56c of the plurality of coaxial cables 56. For example, it is possible to electrically connect the vibrator ground 352b and a ground portion 366 to each other by using a lead wire or the like provided separately from the FPC 360. Moreover, positions where the plurality of individual electrodes 352a and the vibrator ground 352b are disposed are not limited to the positions illustrated in FIG. 11 provided that the positions enable the individual electrodes 352a and the vibrator ground 352b to be connected to the signal wires 56a of the coaxial cables 56 and the grounded portion provided inside the ultrasonic endoscope 312. In other words, the individual electrodes 352a and the vibrator ground 352b may be disposed at the ultrasonic vibrators 348 on the distal end side of the ultrasonic endoscope 312 and may be disposed so as to extend throughout respective entire surfaces of the inside surface and the outside surface of the ultrasonic vibrators 348, or the positions of the individual electrodes 352a and the vibrator ground 352b may be changed, as appropriate, in accordance with the configuration of the ultrasonic observation portion 336.

The FPC 360 of the ultrasonic vibrator unit 346 is disposed along the ultrasonic vibrator array 350, the backing material layer 354, and the cylindrical member 304 that is closer than the backing material layer 354 to the proximal end side of the ultrasonic endoscope 312 (hereinafter also simply referred to as the proximal end side of the backing material layer 354) so as to extend beyond the backing material layer 354. The FPC 360 electrically connects the plurality of individual electrodes 352a and the vibrator ground 352b of the electrode parts 352 and the plurality of coaxial cables 56 to each other. In addition, the FPC 360 has the plurality of electrode pads (not illustrated) disposed on one end side and electrically connected to the plurality of individual electrodes 352a and the vibrator ground 352b of the electrode parts 352; a wiring portion 362 disposed on the proximal end side of the backing material layer 354 and constituted by a plurality of connection portions 364, the plurality of connection portions 364 being a plurality of terminals electrically connected to the signal wires 56a of the plurality of coaxial cables 56; and the ground portion 366 disposed on the other end side, the ground portion 366 being a conductive member electrically connected to the shield layers 56c of the plurality of coaxial cables 56. The FPC 360 that is disposed, as described above, so as to extend along the shape of the ultrasonic vibrator unit 346 on the proximal end side from the electrode parts 352 to the cylindrical member 304 makes a work space for wiring wide and enables a space inside the distal end portion 340 of the ultrasonic endoscope 312 to be effectively used. Moreover, since the FPC 360 is used for wiring to the electrode parts 352, for example, the need of providing a relay point electrically connected to the electrode parts 352 to improve the wiring workability is eliminated, which makes it possible to improve the work efficiency in wiring and further simplify the wiring structure.

A plurality of FPCs 360 may be provided to electrically connect all of the annularly arrayed individual electrodes 352a of the electrode parts 352 and the signal wires 56a of the plurality of coaxial cables 56 to each other via the FPCs 360. When, for example, the plurality of FPCs 360 are disposed, a portion of each FPC 360 on the proximal end side of the backing material layer 354 may have a smooth flat shape. In the example illustrated in FIG. 11, the FPC 360 has a certain thickness; however, the FPC 360 is merely schematically illustrated for description, and, as a matter of course, the dimensional ratio thereof is not an actual dimensional ratio.

Similarly to the first embodiment illustrated in FIG. 4, the heat conductive layer 368 of the ultrasonic vibrator unit is disposed on a surface of the FPC 360 on the backing material layer 354 side and conducts the heat generated in the plurality of ultrasonic vibrators 348 to the ground portion 366 of the FPC 360. The heat conductive layer 368 is preferably disposed so as not to interfere with the plurality of individual electrodes 352a of the electrode parts 352, for example, preferably disposed closer than the electrode parts 352 to the center side of the ultrasonic vibrator unit 346, as illustrated in FIG. 11. The heat conductive layer 368 conducts the heat to the ground portion 366 via a wire (not illustrated) provided inside the FPC 360. As described above, the ultrasonic vibrator unit 346 according to the present embodiment illustrated in FIG. 11 is capable of dissipating the heat generated in the plurality of ultrasonic vibrators 348, via the ground portion 366, to the shield layers 56c of the plurality of coaxial cables 56 electrically connected to the ground portion 366. In the example illustrated in FIG. 11, the heat conductive layer 368 is disposed on a surface of the FPC 360 on the backing material layer 354 side; however, provided that the heat conductive layer 368 is capable of conducting the heat generated from the plurality of ultrasonic vibrators 348, the heat conductive layer 368 may be disposed on a surface of the FPC 360 on the side opposite to the backing material layer 354 or may be disposed on both surfaces thereof.

Meanwhile, the heat conductive layer 368 is disposed at a portion where the FPC 360 is bent along the ultrasonic vibrators 348, the backing material layer 354, and the cylindrical member 304 on the proximal end side of the backing material layer 354. Therefore, the total thickness of the FPC 360 and the heat conductive layer 368 is increased, and the rigidity of the heat conductive layer 368 is added to the FPC 360, which may cause a decrease in workability in disposing the FPC 360 and the heat conductive layer 368 in the ultrasonic vibrator unit 346. In another example according to the present embodiment illustrated in FIG. 12, a heat conductive layer 370 is disposed at only a portion where the FPC 360 is not bent, that is, extends beyond the backing material layer 354, similarly to the example according to the first embodiment illustrated in FIG. 6. As illustrated in FIG. 12, an ultrasonic vibrator unit 369 has a heat conductive member (first heat conductive member) 371 thermally connected at one end to the heat conductive layer 370 and thermally connected at the other end to the plurality of ultrasonic vibrators 348. Therefore, at the portion where the FPC 360 is bent, heat is conducted by the heat conductive member 371, and the heat is conducted to the heat conductive layer 370. Similarly to the heat conductive member 71 according to the first embodiment illustrated in FIG. 6, a highly heat-conductive metal member such as copper, aluminum, gold, or silver, a heat conductive silicone sheet, or the like is usable to constitute the heat conductive member 371. A shape, such as a wire shape, a foil shape, a mesh shape, having flexibility is usable as the shape of the heat conductive member 371 to, for example, improve workability in disposing. Therefore, similarly to the first embodiment illustrated in FIG. 6, it is possible to dissipate the heat generated in the plurality of ultrasonic vibrators 348 to the ground portion 366 and the shield layers 56c of the plurality of coaxial cables 56 by using a simple configuration while improving workability in disposing.

FIG. 12 is simplified for description, and the wiring portion 362 disposed on the same surface of the FPC 360 as the surface on which the ground portion 366 is disposed and the signal wires 56a of the coaxial cables 56 electrically connected to the plurality of connection portions 364 of the wiring portion 362 are omitted. When the heat conductive layer 370 is disposed on the same surface of the FPC 360 as the surface on which the wiring portion 362 is disposed, as is the example illustrated in FIG. 12, it is preferable that the heat conductive layer 370 and the wiring portion 362 be insulated from each other by, for example, disposing the heat conductive layer 370 so as to surround the wiring portion 362, as is in the example according to the first embodiment illustrated in FIG. 8.

Figure 13:
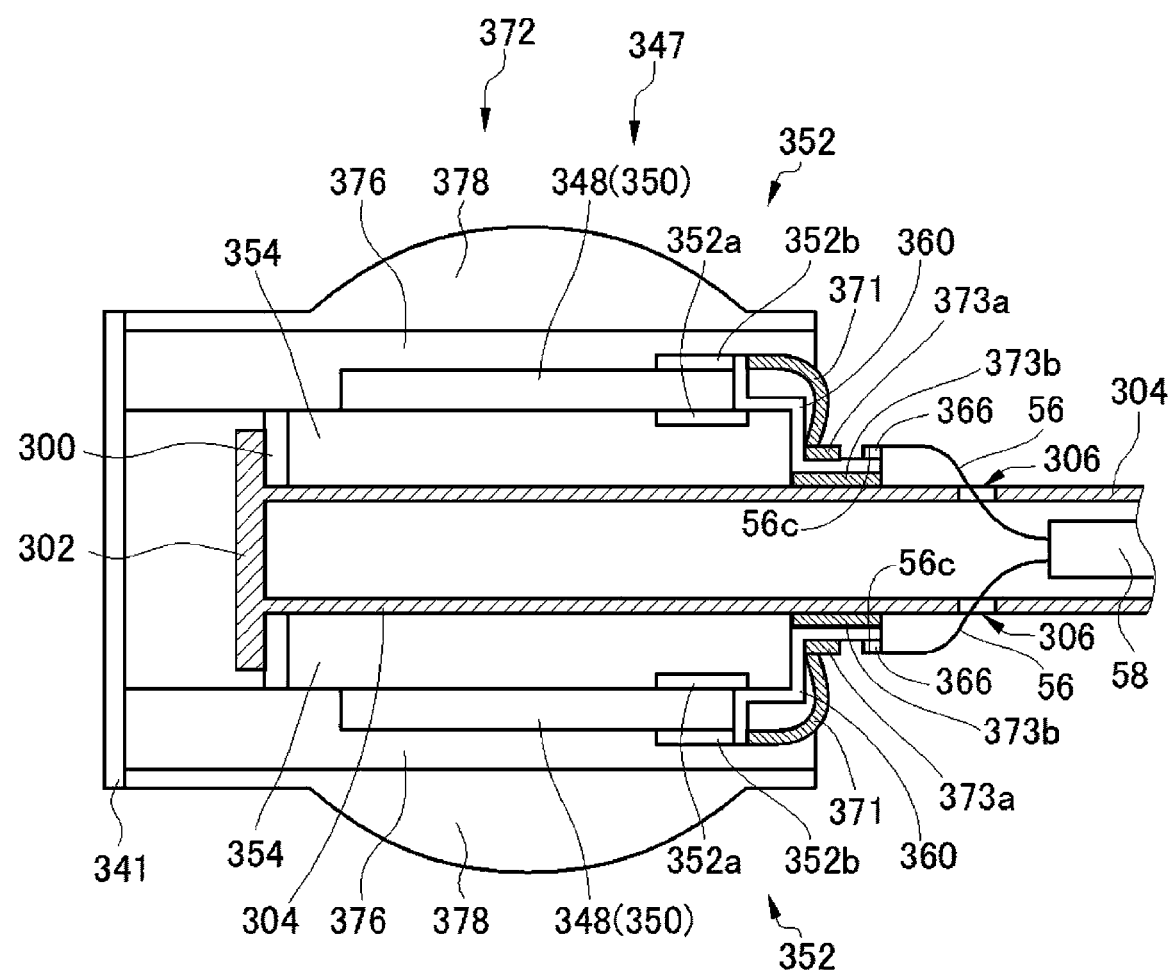
FIG. 13 is a partial longitudinal sectional view of the other example of the ultrasonic vibrator unit illustrated in FIG. 11 and FIG. 12.

In the example according to the present embodiment illustrated in FIG. 12, the heat conductive layer 370 is disposed on the surface of the FPC 360 on the side opposite to the backing material layer 354; however, also in a case in which the ultrasonic vibrator unit 369 has the heat conductive member 371, the heat conductive member 371 may be disposed on the backing material layer 354 side of the FPC 360 provided that it is possible to conduct the heat generated in the plurality of ultrasonic vibrators 348. In FIG. 13, heat conductive layers 373a and 373b are disposed at a flat surface portion where the FPC 360 of an ultrasonic vibrator unit 372 extends beyond the backing material layer 354, similarly to the first embodiment illustrated in FIG. 7, on both surfaces of the FPC 360. In other words, at a flat surface portion of the FPC 360, the heat conductive layer 373a is disposed on the surface on the side opposite to the backing material layer 354 and at an end portion on the heat conductive layer 370 side, and the heat conductive layer 373b is disposed on the entire surface on the backing material layer 354 side. The heat conductive layers 373a and 373b are thermally connected to each other via a wire (not illustrated) provided in an inner portion of the FPC 360. The heat conductive layer 373b and the ground portion 366 of the FPC 360 are thermally connected to each other via the FPC 360, similarly to the other example of the ultrasonic vibrator unit 369 according to the present embodiment illustrated in FIG. 12. Therefore, it is possible to dissipate the heat generated in the plurality of ultrasonic transducers 348 to the ground portion 366 and the shield layers 56c of the plurality of coaxial cables 56 via the heat conductive member 371, the heat conductive layers 373a and 373b, and the FPC 360.

In the example according to the present embodiment illustrated in FIG. 13, the heat conductive layer 373a is disposed at only the end portion on the heat conductive member 371 side; however, the heat conductive layer 373a may be formed so as to extend to the ground portion 366. In this case, it is possible to widen a heat dissipation path to the ground portion 366, and, consequently, it is possible to improve total heat conduction efficiency of the heat conductive layers 373a and 373b, that is, it is possible to improve heat dissipation efficiency. Similarly to FIG. 12, FIG. 13 is simplified for description, and the wiring portion 362, which is provided on the same surface of the FPC 360 as the surface on which the ground portion 366 is provided, and the signal wires 56a of the coaxial cables 56 electrically connected to the plurality of connection portions 364 of the wiring portion 362 are omitted.

Next, referring back to FIG. 11, further description will be provided. As illustrated in FIG. 11, the support plate 302 of the ultrasonic vibrator unit 346 is disposed in contact with a surface of the annular plate 300 on the side opposite to the backing material layer 354. The support plate 302 is a disc-shaped plate material that has an outer diameter larger than the inner diameter of the annular plate 300. The support plate 302 is for fixing the positions of the annular plate 300 and the cylindrical member 304. Therefore, the support plate 302 is preferably joined to the cylindrical member 304 to fix the position at which the cylindrical member 304 is disposed. Accordingly, the support plate 302 may be a member integral with the cylindrical member 304. In addition, when being joined to the cylindrical member 304, the support plate 302 is preferably joined also to the annular plate 300 to fix the position of the cylindrical member 304. The shape of the support plate 302 is not limited to the disc shape and may be an arbitrary shape, such as a polygonal shape, provided that the support plate 302 is capable of fixing the positions of the annular plate 300 and the cylindrical member 304.

The cylindrical member 304 of the ultrasonic vibrator unit 346 is disposed in contact with the inside surface of the backing material layer 354, the inside surface of the annular plate 300, and the surface of the support plate 302 on the side opposite to the distal end side of the ultrasonic endoscope and fixes the laminated body 347. The plurality of coaxial cables 56 covered with the outer sheath 58 are disposed in a space of the cylindrical member 304 on the center side (inner side of the cylindrical member 304) of the ultrasonic vibrator unit 346. The cylindrical member 304 is provided, at a portion on the proximal end side of the backing material layer 354, with a plurality of slits 306 for leading out the plurality of coaxial cables 56 to the outer circumferential side of the cylindrical member 304. The cylindrical member 304 needs only to be capable of supporting the laminated body 347 and may be constituted by an arbitrary member of a metal, a resin, or the like.

An end portion of the FPC 360 on the ultrasonic vibrator array 350 side is provided with the plurality of electrode pads (not illustrated). The plurality of electrode pads of the FPC 360 are a plurality of electrodes electrically connected to the plurality of individual electrodes 352a and the vibrator ground 352b of the electrode parts 352. Among the plurality of electrode pads, the electrode pads that are electrically connected to the plurality of individual electrodes 352a are electrically connected to the plurality of connection portions 364 of the wiring portion 362 via a wire (not illustrated) provided in the FPC 360, and the electrode pad that is electrically connected to the vibrator ground 352b is electrically connected to the ground portion 366 via another wire (not illustrated) provided in the FPC 360. Therefore, the total number of the plurality of electrode pads of the FPC 360 is preferably at least equal to or more than the total number (the number of the channels of the ultrasonic vibrator array 350) of the plurality of ultrasonic vibrators 348.

The wiring portion 362 of the FPC 360 is constituted by the plurality of connection portions 364, which are terminals each wired to a respective one of the signal wires 56a of the plurality of coaxial cables 56. In the example illustrated in FIG. 11, the wiring portion 362 is disposed closer than the ground portion 366 to the distal end side of the ultrasonic vibrator unit 346. The total number of the plurality of connection portions 364 constituting the wiring portion 362 is preferably at least equal to or more than the total number of the plurality of electrode pads (not illustrated) of the FPC 360. When, for example, the number of the channels of the ultrasonic vibrator array 350 is large and may cause a decrease in workability in wiring, the plurality of connection portions 364 may be arrayed in multiple rows. While no illustration is provided, a wiring part between the signal wires of the plurality of coaxial cables 56 and the plurality of connection portions 364 is preferably covered with a filler (not illustrated) such as an insulating resin to suppress the wiring part from disconnecting.

The ground portion 366 of the FPC 360 is a conductive member that is electrically connected to the plurality of electrode pads of the FPC 360 electrically connected to the vibrator ground 352b of the electrode parts 352 and that is electrically connected to the shield layers 56c of the plurality of coaxial cables 56. Therefore, when the shield layers 56c of the plurality of coaxial cables 56 are grounded and when the heat conductive layers 368 (refer to FIG. 11), 370 (refer to FIG. 12), 373a (refer to FIG. 13), 373b (refer to FIG. 13), and the heat conductive member 371 (FIG. 12) are formed of conductive members, it is possible to ground the heat conductive layers 368, 370, 373a, and 373b, which are electrically connected to the ground portion 366, the heat conductive member 371, and the vibrator ground 352b of the electrode parts 352. Consequently, in addition to grounding the vibrator ground 352b, it is possible to suppress noise from outside from being included in ultrasonic echo signals (voltage signals) that the plurality of ultrasonic vibrators 348 receive.

According to the heat dissipation structure provided in the radial-type ultrasonic endoscope 312 according to the third embodiment described above with reference to FIGS. 10 to 13, it is possible to conduct the heat generated in the plurality of ultrasonic vibrators 348 to the ground portion 366 disposed on the FPC 360 by using a simple configuration. Further, since the ground portion 366 is electrically connected to the shield layers 56c of the plurality of coaxial cables 56, the heat conducted to the ground portion 366 is dissipated to the shield layers 56c of the plurality of coaxial cables 56. Therefore, it is possible to efficiently dissipate the heat generated in the plurality of ultrasonic vibrators 348 by using a simple configuration. In addition, forming the heat conductive layers 370 (refer to FIG. 12), 373a (refer to FIG. 13), and 373b (refer to FIG. 13) at only the flat surface portion of the FPC 360 and thermally connecting the heat conductive layers 370, 373a, and 373b and the plurality of ultrasonic vibrators 348 to each other by using the heat conductive member 371 enable the heat dissipation structure to be disposed easily.

An ultrasonic endoscope that has the heat dissipation structure according to the present invention has been described above in detail; however, the present invention is not limited to the above examples and, as a matter of course, may be subjected to various types of improvement or modification within a scope not deviating from the concept of the present invention. Needless to say, it is possible to combine, as appropriate, and use the embodiments and the plurality of examples presented above.

REFERENCE SIGNS LIST 10 ultrasonic inspection system
12, 312 ultrasonic endoscope
14 ultrasonic processor
16 endoscope processor
18 light source device
20 monitor
21a water supply tank
21b suction pump
22 insertion part
24 operating part
26 universal cord
28a air-water supply button
28b suction button
29 angle knob
30 treatment tool insertion port (forceps port)
32a ultrasonic connector
32b endoscope connector
32c light source connector
34a air-water supply tube
34b suction tube
36, 336 ultrasonic observation portion
38, 338 endoscopic observation portion
40, 340 distal end portion
41, 341 exterior member
42 bending portion
43 soft portion
44 treatment tool lead-out port
45 treatment tool channel
46, 69, 72, 246, 346, 369, 372 ultrasonic vibrator unit 47, 347 laminated body
48, 348 ultrasonic vibrator
50, 350 ultrasonic vibrator array
52, 352 electrode part
52a, 352a individual electrode
52b, 352b vibrator ground
54, 354 backing material layer
56 coaxial cables
56a signal wire
56b, 56d, 58 outer sheath
56c shield layer
60, 260a, 260b, 360 flexible printed wiring board (FPC)
62, 362 wiring portion
64, 364 connection portion
66, 366 ground portion
68, 70, 73a, 73b, 74, 273a, 273b, 368, 370, 373a, 373b heat conductive layer
71, 371 heat conductive member (first heat conductive member)
76, 376 acoustic matching layer
78, 378 acoustic lens
80 filler layer
82 observation window
84 objective lens
86 solid-state imaging element
88 illumination windows
90 cleaning nozzle
92 wiring cable
294 second heat conductive member
300 annular plate
302 support plate
304 cylindrical member
306 slit
EL longitudinal direction (elevation direction)
AZ parallel direction (azimuth direction)

What is claimed is:

1. An ultrasonic endoscope comprising:
an ultrasonic vibrator array in which a plurality of ultrasonic vibrators are arrayed;
a backing material layer that supports the plurality of ultrasonic vibrators;
a flexible printed wiring board that extends on a side opposite to the ultrasonic vibrator array with respect to the backing material layer and that comprises a plurality of electrode pads that are each electrically connected to a respective one of the plurality of ultrasonic vibrators of the ultrasonic vibrator array;
a plurality of shield cables that each comprise a signal wire electrically connected to a respective one of the plurality of ultrasonic vibrators and that each comprise a shield member for a respective one of the plurality of signal wires;
a wiring portion that comprises a plurality of connection portions in which the plurality of signal wires of the plurality of shield cables are each electrically connected to a respective one of the plurality of electrode pads of the flexible printed wiring board;
a ground portion that is provided on the flexible printed wiring board and electrically connected to the shield members of the shield cables; and
a heat conductive layer that is provided on at least one surface of the flexible printed wiring board and connected to the ground portion, the heat conductive layer dissipating heat generated in the plurality of ultrasonic vibrators to the ground portion;
wherein the portion of the flexible printed wiring board extending beyond the backing material layer on the side opposite to the ultrasonic vibrator array with respect to the backing material layer is a flat surface portion,
wherein the ground portion is provided on at least one surface of the flat surface portion, and
wherein at least a part of the heat conductive layer is provided on at least one surface of the flat surface portion.

2. The ultrasonic endoscope according to claim 1, wherein the heat conductive layer is provided on at least one surface of the flexible printed wiring board so as to be thermally connected to the plurality of ultrasonic vibrators of the ultrasonic vibrator array and so as to extend beyond the backing material layer from the ultrasonic vibrator array along the backing material layer to the side opposite to the ultrasonic vibrator array with respect to the backing material layer, the heat conductive layer being connected to the ground portion.

3. The ultrasonic endoscope according to claim 2, further comprising a first heat conductive member that thermally connects the plurality of ultrasonic vibrators of the ultrasonic vibrator array and the heat conductive layer to each other.

4. The ultrasonic endoscope according to claim 3,
wherein the heat conductive layer is provided, at the portion of the flexible printed wiring board extending beyond the backing material layer, on only one side of the flat surface portion, and
wherein the first heat conductive member thermally connects, on the one side of the flexible printed wiring board opposite to the backing material layer, the plurality of ultrasonic vibrators and the heat conductive layer to each other.

5. The ultrasonic endoscope according to claim 3,
wherein the heat conductive layer includes two heat conductive layers provided on both surfaces of the flexible printed wiring board,
wherein the first heat conductive member thermally connects, on one side of the flexible printed wiring board opposite to the backing material layer, the plurality of ultrasonic vibrators and the heat conductive layer that is provided on the one side to each other, and
wherein the two heat conductive layers provided on the both surfaces of the flexible printed wiring board are thermally connected to each other.

6. The ultrasonic endoscope according to claim 1, further comprising a first heat conductive member that thermally connects the plurality of ultrasonic vibrators of the ultrasonic vibrator array and the heat conductive layer to each other.

7. The ultrasonic endoscope according to claim 6,
wherein the heat conductive layer is provided, at the portion of the flexible printed wiring board extending beyond the backing material layer, on only one side of the flat surface portion, and
wherein the first heat conductive member thermally connects, on the one side of the flexible printed wiring board opposite to the backing material layer, the plurality of ultrasonic vibrators and the heat conductive layer to each other.

8. The ultrasonic endoscope according to claim 6,
wherein the heat conductive layer includes two heat conductive layers provided on both surfaces of the flexible printed wiring board,
wherein the first heat conductive member thermally connects, on one side of the flexible printed wiring board opposite to the backing material layer, the plurality of ultrasonic vibrators and the heat conductive layer that is provided on the one side to each other, and wherein the two heat conductive layers provided on the both surfaces of the flexible printed wiring board are thermally connected to each other.

9. The ultrasonic endoscope according to claim 1, wherein the heat conductive layer provided on a surface of the flexible printed wiring board on a side where the wiring portion is present is disposed at a portion excluding the plurality of connection portions of the wiring portion so as to surround the plurality of connection portions.

10. The ultrasonic endoscope according to claim 1, wherein the flexible printed wiring board includes a plurality of flexible printed wiring boards disposed on the side opposite to the ultrasonic vibrator array with respect to the backing material layer.

11. The ultrasonic endoscope according to claim 10, further comprising a second heat conductive member that connects the plurality of heat conductive layers that are each provided on a respective one of the plurality of flexible printed wiring boards to each other.

\* \* \* \* \*